(12) United States Patent
Bumpus et al.

(10) Patent No.: US 9,463,173 B2
(45) Date of Patent: Oct. 11, 2016

(54) COMPOSITIONS AND METHODS FOR TREATING OBESITY AND OBESITY-RELATED CONDITIONS

(71) Applicant: THE JOHNS HOPKINS UNIVERSITY, Baltimore, MD (US)

(72) Inventors: Namandje Bumpus, Washington, DC (US); Lindsay Avery, S. Hamilton, MA (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 14/637,784

(22) Filed: Mar. 4, 2015

(65) Prior Publication Data

US 2015/0250747 A1    Sep. 10, 2015

Related U.S. Application Data

(60) Provisional application No. 61/947,537, filed on Mar. 4, 2014.

(51) Int. Cl.
*A01N 37/00* (2006.01)
*A61K 31/19* (2006.01)

(52) U.S. Cl.
CPC .................................. *A61K 31/19* (2013.01)

(58) Field of Classification Search
None
See application file for complete search history.

(56) References Cited

U.S. PATENT DOCUMENTS 6,191,117 B1    2/2001    Kozachuk

FOREIGN PATENT DOCUMENTS

| WO | 0203915 | A2 | 1/2002 |
| WO | 2007009539 | A2 | 1/2007 |
| WO | 2007067341 | A2 | 6/2007 |

OTHER PUBLICATIONS

Ghodke-Puranik, et. al., "Valproic acid pathway: pharmacokinetics and pharmacodynamics" Pharmacogenetics and genomics (2013).*
Silva, M., et al., "Differential effect of valproate and its Delta2- and Delta4-unsaturated metabolites, on the beta-oxidation rate of long-chain and medium-chain fatty acids" Chem Biol Interact. (Sep. 28, 2001) vol. 137, No. 3, pp. 203-212.
Zhang, L, et al., "Combined effects of a high-fat diet and chronic valproic acid treatment on hepatic steatosis and hepatotoxicity in rats", Acta Pharmacol Sin. (Mar. 2014) vol. 35, No. 3, pp. 363-372.
Meral, C., et al., "New adipocytokines (vaspin, apelin, visfatin, adiponectin) levels in children treated with valproic acid" Eur Cytokine Netw. (Jun. 2011) vol. 22, No. 2, pp. 118-122.
Acheampong, A., et al., "Identification of valproic acid metabolites in human serum and urine using hexadeuterated valproic acid and gas chromatographic mass spectrometric analysis", Biomed Mass Spectrom (1983) vol. 10, No. 11, pp. 586-595.
Becker, C., et al., "Influence of valproic acid on hepatic carbohydrate and lipid metabolism", Arch Biochem Biophys (1983) vol. 223, No. 2, pp. 381-392.
Foretz, M., "Metformin inhibits hepatic gluconeogenesis in mice independently of the LKB1/AMPK pathway via a decrease in hepatic energy state" J Clin Invest (Jul. 2010) vol. 120, No. 7, pp. 2355-2369.
Nau, H., et al., "Valproic acid and metabolites: pharmacological and toxicological studies" Epilepsia (1984) vol. 25 (Suppl. 1), S14-S22.
Shaw, R., "The kinase LKB1 mediates glucose homeostasis in liver and therapeutic effects of metformin", Science, (Dec. 9, 2005) vol. 310, pp. 1642-1646.
Silva, M., "Valproic acid metabolism and its effects on mitochondrial fatty acid oxidation: a review" J Inherit Metab Dis, (2008) vol. 31, pp. 205-216.
Sztajnkrycer, M., "Valproic acid toxicity: overview and management" J Toxicol Clin Toxicol, (2002) vol. 40, No. 6, pp. 789-801.

* cited by examiner

*Primary Examiner* — Jeffrey H Murray
(74) *Attorney, Agent, or Firm* — Johns Hopkins Technology Transfer

(57) ABSTRACT

The present invention relates to the field of obesity. More specifically, the present invention provides methods and compositions useful in treating obesity and obesity-associated conditions. In one embodiment, a method for treating obesity in a subject comprises the step of administering an effective amount of valproic acid (VPA) or an analog, derivative or metabolite thereof to the subject.

6 Claims, 15 Drawing Sheets

COMPOSITIONS AND METHODS FOR TREATING OBESITY AND OBESITY-RELATED CONDITIONS

CROSS-REFERENCE TO RELATED APPLICATIONS

This application claims priority to U.S. Provisional Patent Application Ser. No. 61/947,537, filed Mar. 4, 2014, which is incorporated herein by reference in its entirety.

STATEMENT OF GOVERNMENTAL INTEREST

This invention was made with government support under grant no. R01GM103853, awarded by the National Institutes of Health. The government has certain rights in the invention.

FIELD OF THE INVENTION

The present invention relates to the field of obesity. More specifically, the present invention provides methods and compositions useful in treating obesity and obesity-associated conditions.

BACKGROUND OF THE INVENTION

Obesity has become a global epidemic afflicting both children and adults, and gradually spreading from the Western countries to the developing nations as well. It is now widely recognized that obesity is associated with, and is actually a major culprit in, numerous comorbidities such as cardiovascular diseases (CVD), type 2 diabetes, hypertension, certain cancers, and sleep apnea/sleep-disordered breathing. As recently acknowledged by a joint American Heart Association and American Diabetes Association (AHA/ADA) statement, obesity is an independent risk factor for CVD, and CVD risks have also been documented in obese children. Obesity is associated with an increased risk of overall morbidity and mortality as well as reduced life expectancy. Indeed, obesity and overweight are now listed as independent cardiovascular risk factors in the joint AHA/ADA call for the prevention of cardiovascular disease and diabetes.

With the exception of bariatric surgery, which can only be offered to a limited number of subjects, the lack of any truly effective treatment for obesity highlights the gravity of current prospects to control the obesity epidemic. Preventive measures have generally failed; effective public and political strategies to reshape lifestyle by proper nutrition and exercise so as to counteract the global obesity trends have not yet been formulated. Finally, the current generation of weight-reducing medications offers limited benefit, and indeed, despite more than a decade of use has failed to impact the global obesity challenge. Health service use and medical costs associated with obesity and related diseases have risen dramatically and are expected to continue to rise. Accordingly, novel therapeutic strategies to combat obesity are needed.

SUMMARY OF THE INVENTION

The present invention is based, at least in part, on the discovery that valproic acid (VPA) is a novel activator of AMP-activated protein kinase (AMPK), a key regulator of cellular metabolism, using primary mouse and human hepatocytes. As described herein, incubation of primary mouse hepatocytes with VPA resulted in increased levels of phosphorylated AMPK and acetyl-CoA carboxylase (ACC). This finding was recapitulated using primary human hepatocytes. Pretreatment of mouse hepatocytes with a small-molecule inhibitor of AMPK, Compound C (6-[4-(2-piperidin-1-ylethoxy)phenyl]-3-pyridin-4-ylpyrazolo[1,5-a]pyrimidine), abrogated the phosphorylation of ACC following treatment with VPA. The cytochrome P450 inhibitor 1-aminobenzotriazole blocked the VPA-stimulated phosphorylation of AMPK, suggesting a requirement for biotransformation of VPA. In line with this, treatment of hepatocytes with metabolites of VPA resulted in increased phosphorylation of AMPK/ACC as compared with VPA. Treatment of ob/ob mice with VPA for 14 days resulted in decreased liver masses, hepatic fat accumulation, and serum glucose. These results paralleled those observed in mice treated with metformin. In addition, a targeted mass spectrometry-based metabolomics assay revealed several small molecules that were differentially abundant in the serum of ob/ob mice treated with VPA as compared with vehicle-treated mice. These studies are the first to establish VPA and its metabolites as in vitro activators of AMPK.

Accordingly, in one aspect, the present invention provides methods for treating obesity and obesity-associated conditions. In particular embodiments, a method for reducing hepatic fat accumulation and serum glucose in a subject comprising the step of administering an effective amount of valproic acid (VPA) or metabolite thereof to the subject. In other embodiments, a method for treating obesity in a subject comprises the step of administering an effective amount of valproic acid (VPA) or an analog, derivative or metabolite thereof to the subject. In yet another embodiment, a method for treating type 2 diabetes in a subject comprises the step of administering an effective amount of valproic acid (VPA) or an analog, derivative or metabolite thereof to the subject. In certain embodiments, the VPA metabolite is one or more of 2-ene-VPA, 4-ene-VPA, 3-OH-VPA, and 3-keto-VPA. In a specific embodiment, the VPA metabolite is 4-ene VPA. In certain embodiments, the VPA metabolite is administered at a lower dose than the recommended VPA dose.

DETAILED DESCRIPTION OF THE INVENTION

Figure 1A:
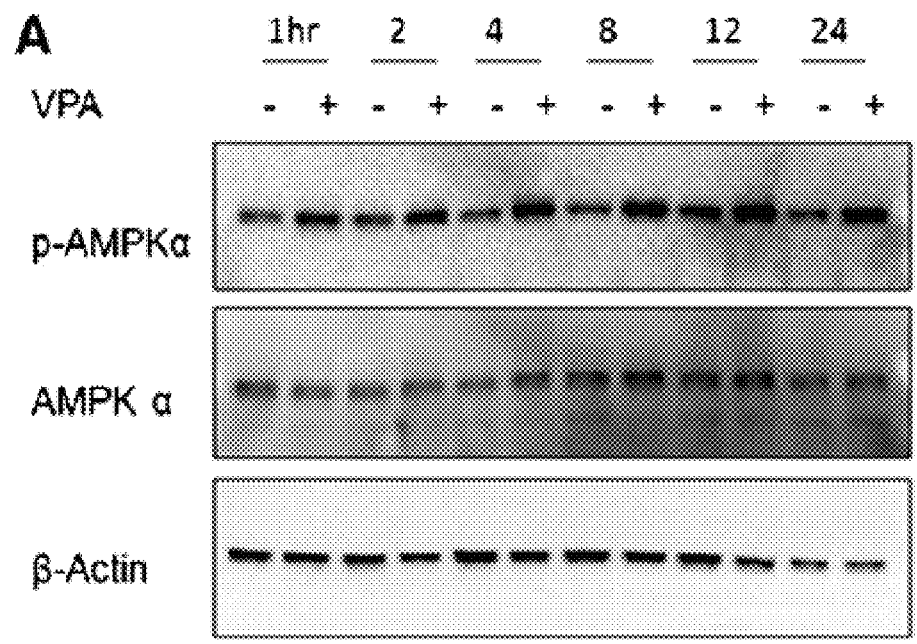
FIG. 1A-1C. VPA treatment results in increased levels of phosphorylated AMPK/ACC in primary mouse hepatocytes. Primary mouse hepatocytes were treated with vehicle or 800 mMVPA for the indicated time points and immunoblotted for p-AMPKa, AMPKa, p-ACC, ACC, and b-actin (A and B). Dose-dependence of levels of p-AMPKa and p-ACC in response to VPA were measured following 2-hour treatment with either vehicle or 200, 400, and 800 mM, and 1.2 or 2 mM of VPA (C). Immunoblots shown in A and C are representative of four independent experiments and hepatocyte isolations.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

Metabolic disorders, encompassing diabetes and obesity, are an ongoing epidemic and are rapidly becoming one of the largest public health challenges. Characterized by elevated serum glucose, increased cholesterol and triglycerides, and insulin resistance, metabolic disorders result in increased risk of cardiovascular disease, hypertension, stroke, and many other health concerns. As such, there is a need for new and efficacious therapies to biochemically treat metabolic disorders. A number of drugs used for treating metabolic disorders, including metformin and thiazolidinediones, have been demonstrated to act at least in part through the activation of AMP activated protein kinase (AMPK).

AMPK is a heterotrimeric serine/threonine kinase that has been demonstrated to play a key role in the regulation of cellular energy metabolism. In response to a reduction in cellular energy resulting from cellular or metabolic stresses, AMPK inhibits anabolic pathways that consume ATP and activates catabolic pathways that produce ATP to re-establish the cellular energy homeostasis (Kahn et al., 2005). Activation occurs via phosphorylation of the a subunit (Thr172) and subsequently phosphorylates and inactivates acetyl-CoA carboxylase (ACC), the enzyme that catalyzes the formation of malonyl-CoA via carboxylation of acetyl-CoA, resulting in diminished biosynthesis of fatty acids and stimulation of fatty acid oxidation (Bonnefont et al., 2004).

To this end, AMPK has become an attractive therapeutic target in the treatment of metabolic disorders, including type 2 diabetes and obesity (Winder and Hardie, 1999).

Valproic acid (VPA) is one of the most commonly prescribed antiepileptic drugs and has also been found effective for the treatment of bipolar disorders and migraine headaches. In addition, VPA is currently under investigation as a histone deacetylase (HDAC) inhibitor for the treatment of human immunodeficiency virus and various cancers (Nau and Loscher, 1984; Phiel et al., 2001). VPA is extensively metabolized by the cytochromes P450 and via b-oxidation, and many of its primary metabolites have been demonstrated to have antiepileptic efficacy (Nau and Loscher, 1984). Several of these metabolites of VPA, including 2-ene-VPA, 4-ene-VPA, 3-OH-VPA, and 3-keto-VPA, have 2-ene-VPA, 4-ene-VPA, 3-OH-VPA, and 3-keto-VPA been detected in the circulating plasma following dosing of VPA (Nau and Löscher, 1982; Acheampong et al., 1983). VPA has also been demonstrated to affect carbohydrate and lipid metabolism by a decreased rate of fatty acid synthesis, decreased cellular acetyl-CoA, and decreased cellular citrate (Becker and Harris, 1983). In addition, VPA has been shown to decrease the rate of glucose-6-phosphate dehydrogenase and glutathione peroxidase activity (Cotariu et al., 1990). These studies combined suggest that VPA may have an impact on the regulation of cellular metabolism.

In the present study, we demonstrate that VPA, as well as the cytochrome P450- and b-oxidation-dependent metabolites of VPA, activate AMPK in vitro, and that in vivo treatment with VPA results in significantly decreased liver mass/fat content and serum glucose in ob/ob mice. In addition, utilizing a targeted metabolomics approach, we have identified several endogenous small molecules that may be modulated in response to VPA. Targeted metabolomics is a powerful approach to probing changes in the endogenous cellular metabolome. As opposed to global metabolomics, targeted metabolomics is designed to identify a defined set of components of biochemical pathways of interest and allows for greater sensitivity and selectivity. As such, we have designed an ultra-high-performance liquid chromatography-tandem mass spectrometry (uHPLC-MS/MS) method for characterizing the levels of endogenous small molecules that play key roles in the tricarboxylic acid cycle, glycolysis, the urea cycle, the glutathione pathway, and the pentose phosphate pathway, as well as amino acids and nucleoside bases. This study is the first to define VPA as an activator of AMPK and to demonstrate the ability of VPA to decrease liver mass/fat content and serum glucose in vivo in ob/ob mice.

Accordingly, in various embodiments, the present invention provides methods for administering valproic acid (VPA), or analogs or derivatives thereof, to patients having obesity, type 2 diabetes, and other obesity-related conditions. VPA and the family of valproate salts are structurally simple drugs that possess a wide range of pharmacological activities. VPA compounds are among the few broad-spectrum anticonvulsants that are effective in both partial and generalized seizures. VPA and the related valproate salts are first line drugs of choice for epilepsy, bipolar disorder, and migraine prophylaxis.

VPA and analogs or derivatives thereof are known in the art. See, e.g., PCT Publication No. WO/2009/142968, WO/2007/015724, and WO/2004/054957; U.S. Patent Application Publication Nos. US2013/0029924, US2012/0142658, US2012/0059060, US2007/0098786, US2006/0263437, and US2006/0223888; U.S. Pat. No. 5,019,398, U.S. Pat. No. 5,017,613, U.S. Pat. No. 5,049,586, U.S. Pat. No. 4,913,906, U.S. Pat. No. 4,895,873, U.S. Pat. No. 4,699,927, U.S. Pat. No. 4,558,070, and U.S. Pat. No. 4,292,425. Methods for making VPA, analogs and derivatives thereof are also known in the art. See, e.g., U.S. Pat. No. 5,440,023, U.S. Pat. No. 5,185,159, and U.S. Pat. No. 5,101,070; U.S. Patent Application Publication No. US2011/0040122; and PCT Publication No. WO/2008/062471.

As used herein, an "analog" or "analogue" refers to a compound which is sufficiently homologous or structurally and chemically similar to a compound such that it has a similar functional activity for a desired purpose as the original compound. Analogues include polypeptides having one or more amino acid substitutions compared with a particular substance. Analogues of valproic acid include valnoctamide and those disclosed in U.S. Patent Application Publication No. US2006/0223888.

A "derivative," as used herein, refers to a form of a substance, such as valproic acid, which has at least one functional group altered, added, or removed, compared with the parent compound. Derivatives include, for example, esterified acids and salts. Thus, sodium valproate is a derivative of valproic acid.

In some embodiments, derivatives may be a prodrug of the active agent. For example esters and amine derivatives of valproic acid may be bioconverted to valproic acid. Examples of such derivatives include valpromide, butyl valproate, hexyl valproate, isoamyl valproate, isobutyl valproate, propyl valproate sodium valproate, 2-propylpentanol-di-n-propylacetate, glycerol tri-dipropylacetate, di sodium valproate, and 1'-ethoxycarbonyloxyethyl ester of valproic acid. Prodrugs may be beneficial for a number of reasons, including enhanced solubility, lower toxicity, or for use in extended release compositions.

The present invention also provides methods for administering metabolites of VPA. In one embodiment, the VPA metabolite is 3-OH-VPA (also known as 3-Hydroxy Valproic Acid; 2-Propyl-3-hydroxypentanoic Acid; and 3-Hydroxy-2-propylpentanoic Acid). In a further embodiment, the VPA metabolite is 3-keto-VPA (also known as 3-Keto Valproic Acid Sodium Salt; 3-oxo-2-propyl-pentanoic Acid Sodium Salt; 2-Propyl-3-oxopentanoic Acid Sodium Salt; 3-Oxo-dipropylacetic Acid Sodium Salt; and 3-Oxovalproic Acid Sodium Salt). In an alternative embodiment, the VPA metabolite is 2-ene-VPA (also known as (E,Z) 2-Propyl-2-pentenoic Acid; 2-Propyl-2-pentenoate; and 2-propyl-penten-2-oic Acid). In yet another embodiment, the VPA metabolite is 4-ene-VPA (also known as (+/−)-2-Propyl-4-pentenoic Acid; 2-Allylpentanoic Acid; and 2-n-Propyl-4-pentenoic Acid). In another embodiment, the VPA metabolite is 5-OH-VPA (also known as 5-Hydroxy Valproic Acid Sodium Salt; 5-Hydroxy-2-propylpentanoic Acid; 2-Propyl-5-hydroxypentanoic Acid Sodium Salt; and 2-n-Propyl-5-hydroxypentanoic Acid Sodium Salt). In other embodiments, the VPA metabolite can be 5-OH-VPA-d7 (also known as 5-Hydroxy Valproic Acid-d7 Sodium Salt; 5-Hydroxy-2-(propyl-d7)pentanoic Acid; 2-(Propyl-d7)-5-hydroxypentanoic Acid Sodium Salt; and 2-n-(Propyl-d7)-5-hydroxypentanoic Acid Sodium Salt); VPA 985 (also known as Lixivaptan; N[3-Chloro-4-(5H-pyrrolo[2,1-c][1,4]benzo-diazepin-10(11H)-ylcarbonyl)phenyl]-5-fluoro-2-methyl-benzamide; and WAY-VPA 985); 2,4-diene-VPA ((E,Z)-2-Propyl-2,4-pentadienoic Acid); VPA-G (also known as Valproic Acid β-D-Glucuronide; 1-(2-Propylpentanoate) β-D-Glucopyranuronic Acid; 1-O-Valproyl-β-D-glucopyranuronic Acid; Dipropylacetate Glucuronide; Valproate Glucuronide; and Valproic Acid Glucuronide); VPA-G-d6 (also known as Valproic Acid-d6 β-D-Glucuronide; 1-(2-Propylpentanoate-d6) β-D-Glucopyranuronic Acid; 1-O-(Valproyl-d6)-β-D-glucopyranuronic Acid; Dipropylacetate-d6 Glucuronide; Valproate-d6 Glucuronide; and Valproic Acid-d6 Glucuronide). The present invention contemplates the use of any one or more of VPA, analogs, metabolites or derivatives thereof.

The terms "patient," "individual," or "subject" are used interchangeably herein, and refer to a mammal, particularly, a human. The patient may have mild, intermediate or severe disease. The patient may be treatment naïve, responding to any form of treatment, or refractory. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates.

As used herein, the terms "treatment," "treating," "treat" and the like, refer to obtaining a desired pharmacologic and/or physiologic effect. The terms are also used in the context of the administration of a "therapeutically effective amount" of an agent, e.g., an VPA, or an analog, metabolite or derivative thereof. The effect may be prophylactic in terms of completely or partially preventing a particular outcome, disease or symptom thereof and/or may be therapeutic in terms of a partial or complete cure for a disease/condition and/or adverse effect attributable to the disease/condition. "Treatment," as used herein, covers any treatment of a disease or condition in a subject, particularly in a human, and includes: (a) preventing the disease or condition from occurring in a subject which may be predisposed to the disease or condition but has not yet been diagnosed as having it; (b) inhibiting the disease or condition, i.e., arresting its development; and (c) relieving the disease or condition, e.g., causing regression of the disease or condition, e.g., to completely or partially remove symptoms of the disease or condition. In particular embodiments, the term is used in the context of treating a subject or patient having obesity, type 2 diabetes or a condition associate with obesity.

As used herein, the term "ameliorating," with reference to a condition, refers to any observable beneficial effect of the treatment. The beneficial effect can be evidenced, for example, by a delayed onset of clinical symptoms of the condition in a susceptible subject, a reduction in severity of some or all clinical symptoms of the condition, a slower progression of the condition, a reduction in the number of relapses of the condition, an improvement in the overall health or well-being of the subject, by other parameters well known in the art that are specific to the particular condition, and combinations of such factors. For example, ameliorating, in some embodiments of the disclosed method, refers to delaying progression of obesity or eliminating or reducing the severity of one or more obesity symptoms.

"Administering" includes routes of administration which allow the compositions of the present invention to perform their intended function, e.g., treating obesity, type 2 diabetes or obesity-associated conditions. A variety of routes of administration are possible including, but not limited to, parenteral (e.g., intravenous, intraarterial, intramuscular, subcutaneous injection), oral (e.g., dietary), inhalation (e.g., aerosol to lung), topical, nasal, rectal, or via slow releasing microcarriers depending on the disease or condition to be treated. In particular embodiments, the route of administration is oral. Formulation of the compound to be administered will vary according to the route of administration selected (e.g., solution, emulsion, gels, aerosols, capsule). An appropriate composition can be prepared in a physiologically acceptable vehicle or carrier and optional adjuvants and preservatives. For solutions or emulsions, suitable carriers include, for example, aqueous or alcoholic/aqueous solutions, emulsions or suspensions, including saline and buffered media, sterile water, creams, ointments, lotions, oils, pastes and solid carriers. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers. See generally, Remington's Pharmaceutical Science, 16th Edition, Mack, Ed. (1980)).

An "effective amount" includes those amounts of the composition of the present invention which allow it to perform its intended function, e.g., treating or preventing, partially or totally, obesity, type 2 diabetes, or obesity-associate conditions as described herein. The effective amount will depend upon a number of factors, including biological activity, age, body weight, sex, general health, severity of the condition to be treated, as well as appropriate pharmacokinetic properties. A therapeutically effective amount of a composition of the present invention can be administered by an appropriate route in a single dose or multiple doses. Further, the dosages of the composition can be proportionally increased or decreased as indicated by the exigencies of the therapeutic or prophylactic situation.

For example, dosages of VPA, an analog or derivative thereof may be from about 0.01 mg/kg/day to about 100 mg/kg/day, from about 0.1 mg/kg/day to about 50 mg/kg/day, or from about 1 mg/kg/day to about 30 mg/kg/day. VPA, an analog or derivative thereof can be administered at a dosage of about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg/day. For example, VPA, an analog or derivative thereof is delivered to a subject in need thereof at a dosage of from about 1 mg/kg/day to about 30 mg/kg/day, about 5 to about 25 mg/kg/day, about 5 to about 20 mg/kg/day, about 5 to about 15 mg/kg/day, about 7 to about 13 mg/kg/day, or any range or value in between.

In other embodiments, VPA, analog or derivative thereof is administered in an amount, range, value or fraction of the foregoing, or to achieve a serum concentration of about 100 to about 1500 μM, about 200 to about 1400 μM, about 300 to about 1300 μM, about 300 to about 1200 μM, about 300 to about 1100 μM, or about 400 to about 1000 μM. More specifically, an amount sufficient to achieve a serum concentration of about 100, 150 200, 250, 300, 350, 400, 450, 500, 550, 600, 650, 700, 750, 800, 850 900, 950, 1000, 1050, 1100, 1150, 1200, 1250, 1300, 1350, 1400, 1450, 1500, 1600, 1700, 1800, 1900, or 2000, μM. In a specific embodiment, VPA, analog or derivative thereof is administered in an amount sufficient to achieve a serum concentration of about 400 to about 100004. In other embodiments, the VPA, analog or derivative thereof is administered in an amount sufficient to achieve a serum concentration of about 400 to about 900 μM, about 450 to about 850 μM, about 500 to about 800 μM, about 550 to about 750 μM, or about 600 to about 700 μM.

As described herein, metabolites of VPA can be administered in a much smaller dose than is usually given for VPA itself. In particular embodiments, VPA metabolites are administered at about ½, ⅓, ¼, ⅕, ⅙, ⅐, ⅛, ⅑, ⅒, 1/11, 1/12, 1/13, 1/14, 1/15, 1/16, 1/17, 1/18, 1/19, 1/20, 1/21, 1/22, 1/23, 1/24, 1/25, 1/26, 1/27, 1/28, 1/29, 1/30, 1/31, 1/32, 1/33, 1/34, 1/35, 1/36, 1/37, 1/38, 1/39, 1/40, 1/41, 1/42, 1/43, 1/44, 1/45, 1/46, 1/47, 1/48, 1/49 or 1/50$^{th}$ a dose of VPA itself. In particular embodiments, VPA metabolites are administered in range of about 1/10 to about 1/60, about 1/20 to about 1/50, about 1/30 to about 1/45, or about 1/35 to about 1/45 of a typical VPA amount. Thus, in certain embodiments, VPA metabolites can be administered in an amount of about 100 to about 400, about 150 to about 350, about 200 to about 300 µg/kg/day.

In particular embodiments, VPA metabolites are administered in an amount of about 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, or 400 µg/kg/day.

In other embodiments, VPA metabolite(s) are administered in an amount, range, value or fraction of the foregoing, or to achieve a serum concentration of about 1 to about 100, more specifically, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 µM. In other embodiments, VPA metabolites are administered in an amount sufficient to achieve a serum concentration of about 1 to about 50, about 5 to about 45, about 5 to about 40, about 5 to about 35, about 5 to about 30, about 5 to about 25, about 10 to about 35, about 10 to about 30, about 10 to about 25 µM.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term "about."

It is shown herein that valproic acid can be used to treat obesity. Generally, the present disclosure provides embodiments of a method for treating obesity in a subject by administering to the subject a therapeutically effective amount of an active agent or composition of the active agent. The active agent is selected from VPA, a VPA derivative, a VPA analog or a VPA metabolite. In one embodiment, administration of VPA, a VPA derivative, a VPA analog, or a VPA metabolite, treats obesity in a subject. For example, the disclosed methods can reduce weight, for example, by at least 10%, at least 20%, at least 30%, at least 40%, at least 50%, such as about 5% to about 90%, including about 10% to about 70% percent, about 20% to about 50% (e.g., 10%, 20%, 30%, 40%, 50%, 60%, 70%, 80% or 90%) as compared to weight levels prior to treatment or a standard reference value.

In some embodiments, following the administration of one or more therapies, obese subjects are monitored to determine the response to the therapy. For example, subjects are monitored to determine if the therapy resulted in a reduction of weight or some other parameter of weight loss. In particular examples, subjects are analyzed one or more times, starting one or more days following treatment. Subjects can be monitored using any method known in the art. In particular examples, if subjects are stable or have a minor, mixed or partial response to treatment, they can be re-treated after re-evaluation with the same schedule and preparation of compositions that they previously received for the desired amount of time, such as for at least three months, at least six months, at least twelve months, or at least twenty-four months of total treatment.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Chemicals and Reagents.

Valproic acid sodium salt was obtained from Sigma-Aldrich (St. Louis, Mo.). 2-Ene-VPA, 4-ene-VPA, 3-OH-VPA, and 3-keto-VPA were obtained from Toronto Research Chemicals, Inc. (Toronto, ON, Canada). Metformin (Glucophage) and VPA (Depakote) for use in the animal study were obtained from the Johns Hopkins Hospital pharmacy supply store (Baltimore, Md.). Compound C (6-[4-(2-piperidin-1-ylethoxy)phenyl]-3-pyridin-4-ylpyrazolo[1,5-a]pyrimidine) was purchased from Calbiochem of EMD Millipore (EMD Millipore, Billerica, Mass.). 1-Aminobenzotriazole was purchased from Sigma-Aldrich.

Isolation of Primary Mouse Hepatocytes.

Primary murine hepatocytes were isolated from 9-12-week-old male C57BL/6 mice obtained from The Jackson Laboratories (Bar Harbor, Me.) via collagenase liver perfusion as previously described (Lee et al., 2004). Hepatocytes were plated in Williams' E medium supplemented with 5% fetal bovine serum (FBS), penicillin, streptomycin, and L-glutamine. Following incubation of cultures for 24 hours, medium was refreshed 4 hours prior to the treatment of hepatocytes with 800 mM of VPA or 20 mM of 2-ene-VPA, 4-ene-VPA, 3-OH-VPA, 3-keto-VPA or vehicle solvent (dimethylsulfoxide or water). For inhibition experiments, hepatocytes were preincubated with 10 mM Compound C for 30 minutes (Hsu et al., 2011), and 1 mM 1-aminobenzotriazole for 1 hour prior (Bumpus, 2011).

Primary Human Hepatocytes.

Primary human hepatocytes were obtained from Xeno-Tech LLC (Lenexa, Kans.). Four preparations were used: male, 55 years old; female, 43 years old; female, 59 years old; and male, 36 years old. The hepatocytes had reported viabilities of 95.4, 74.7, 77.9, and 74.9%, respectively. Upon receipt, the shipping medium was changed to Williams' E medium containing 10% FBS, penicillin, streptomycin, and L-glutamine. Following 24 hours of incubation at 37° C. and 5% CO2, the media was changed to 5% FBS, penicillin, streptomycin, and L-glutamine 4 hours prior to treatments. Hepatocytes were then incubated with 800 mM of VPA.

Immunoblot Analysis.

Cells were harvested as previously described (Bumpus, 2011). Proteins (20 mg) were resolved by sodium dodecyl sulfate polyacrylamide gel electrophoresis, electrotransferred to a nitrocellulose membrane, and probed using antibodies against AMPKa, phosphorylated (p-) AMPKa (Thr172), ACC, p-ACC (Ser79), and b-actin (obtained from Cell Signaling Technology, Danvers, Mass.).

HDAC Activity Assay.

Analysis of HDAC activity was performed using an HDAC activity fluorometric assay kit (Caymen Chemicals, Ann Arbor, Mich.) and was carried out according to the manufacturer's instructions. Crude nuclear extracts were prepared from primary mouse hepatocytes as described in the manufacturer's instructions.

In Vivo Mouse Study.

All treatments of mice as a part of this study were in accordance with protocols that were approved by the Institutional Animal Care and Use Committee of The Johns Hopkins University School of Medicine. Mice (8-9 weeks old) homozygous for the leptin obese mutation (B6.V-Lepob/J; herein denoted as ob/ob mice) were purchased from The Jackson Laboratories. Metformin was used as a positive control for comparison of VPA treatment in this study, since it has been shown previously to improve the obese phenotype of ob/ob mice. Administration of VPA and metformin was carried out via dissolution in the animals' drinking water for consumption over a period of 14 days. This method has been previously used for administration of metformin and VPA (Nau and Löscher, 1982, 1984; Sugai et al., 2004; Ma et al., 2007; Phoenix et al., 2009). Body masses were recorded on day 1 prior to treatment, day 7, and day 14. After 14 days of drug treatments, all mice were euthanized by isoflurane inhalation followed by cervical dislocation, and whole blood was collected immediately. The livers were weighed immediately, rinsed in cold phosphate-buffered saline, and fixed in 10% formalin for 48 hours for hematoxylin and eosin staining.

Serum Glucose and Triglycerides.

Serum glucose was analyzed using a Colorimetric Glucose Assay obtained from BioVision, Inc. (Milpitas, Calif.) and was performed according to manufacturer's instructions. Serum triglycerides were analyzed utilizing a Serum Triglyceride Determination Kit obtained from Sigma-Aldrich and was performed according to manufacturer's instructions.

uHPLC-MS/MS Targeted Metabolomics.

Serum from each mouse was analyzed using a targeted uHPLC-MS/MS metabolomics method designed to detect endogenous biochemical pathway intermediates. The uHPLC-MS/MS assay is composed of separate positive ion and negative ion mode methods to detect 32 biochemical metabolites of the tricarboxylic acid cycle, glutathione pathway, pentose phosphate pathway, and glycolysis, as well as amino acids and nucleotides. The instrumentation was composed of a Thermo Scientific TSQ Vantage Triple Stage Quadrupole mass spectrometer interfaced with a Dionex UltiMate 3000 uHPLC system (Thermo Scientific, Waltham, Mass.). Optimal parent mass, product ion transitions, and collision energies were determined for each molecule using synthetic standards. Resolution and sample preparation was performed as previously described (Lade et al., 2013). Table 1 details the compounds analyzed, respective selected reaction monitoring transitions, collision energies, and retention times.

Results

VPA Stimulates Phosphorylation of AMPK and ACC in Hepatocytes

Figure 1B:
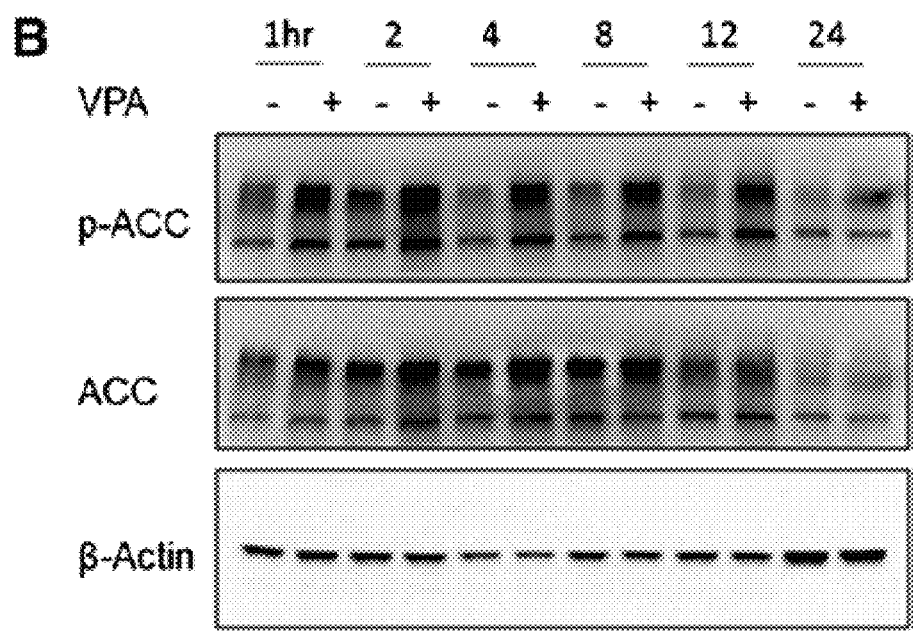
Figure 1C:
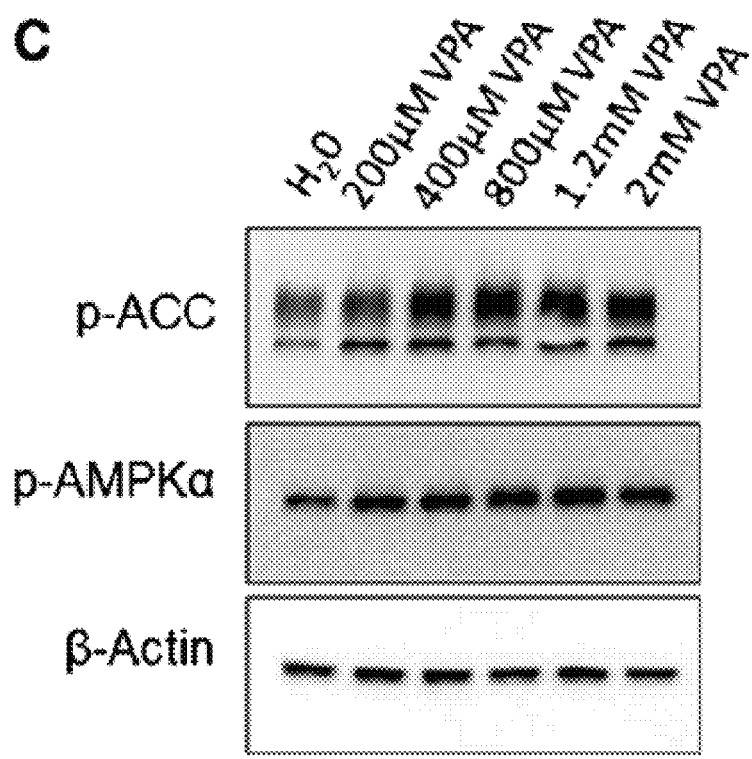
Figure 2A:
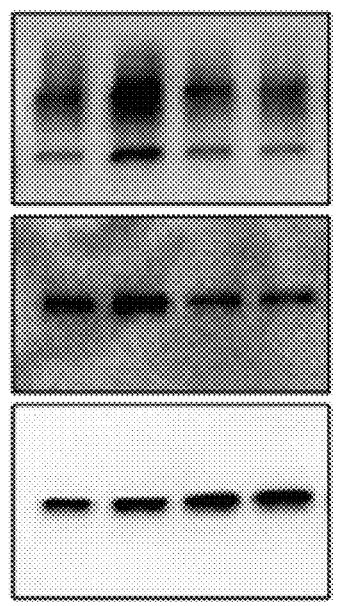
FIG. 2A-2C. Phosphorylation of ACC following VPA treatment is AMPK dependent. Hepatocytes were incubated with 10 mM Compound C for 30 minutes prior to treatment with 800 mM VPA for 2 hours and immunoblotted for p-AMPKa, p-ACC, and b-actin (A). Immunoblots shown are representative of four independent experiments and hepatocyte isolations. Densitometry analyses were performed and are reported as the mean 6 S.D. of samples from four independent experiments using the treatment combinations indicated in B and C. Student's t tests were performed comparing the fold change of VPA versus vehicle and the fold change of Compound C+VPA versus Compound C alone to determine significance. *P , 0.05; **P , 0.01. DMSO, dimethylsulfoxide.
Figure 2B:
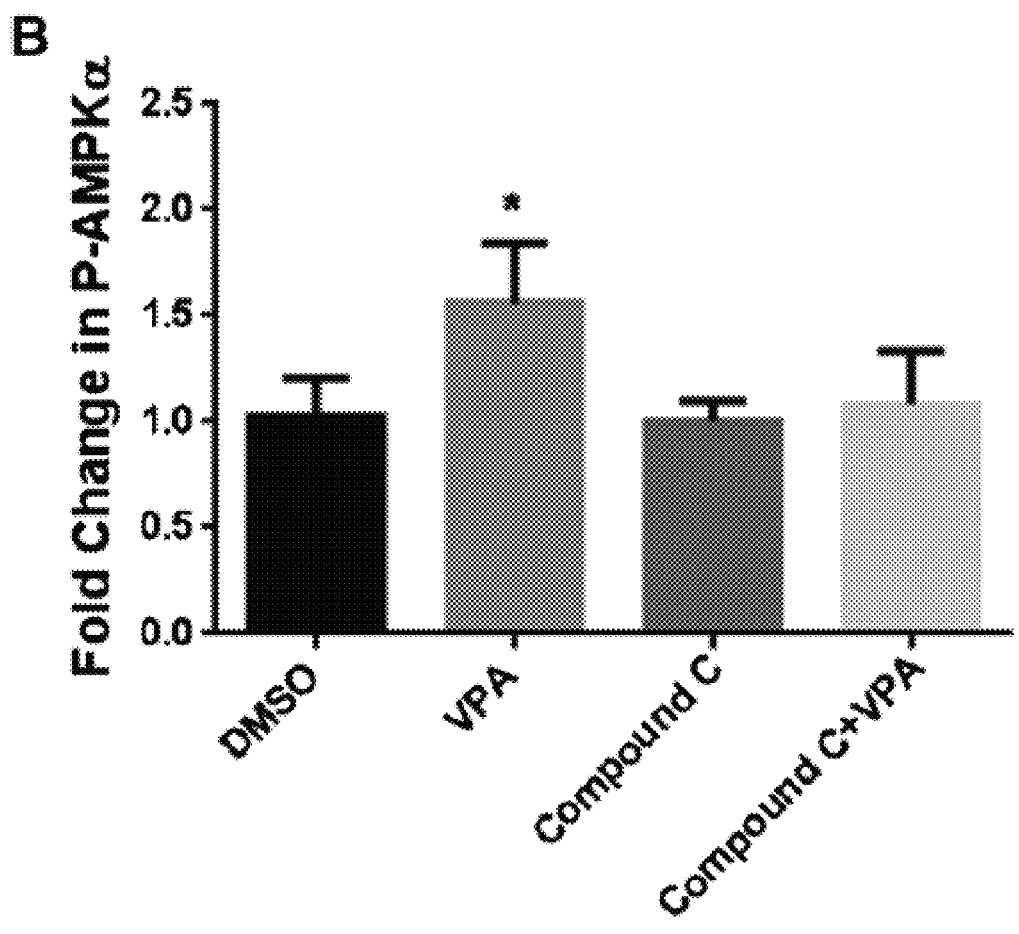
Figure 2C:
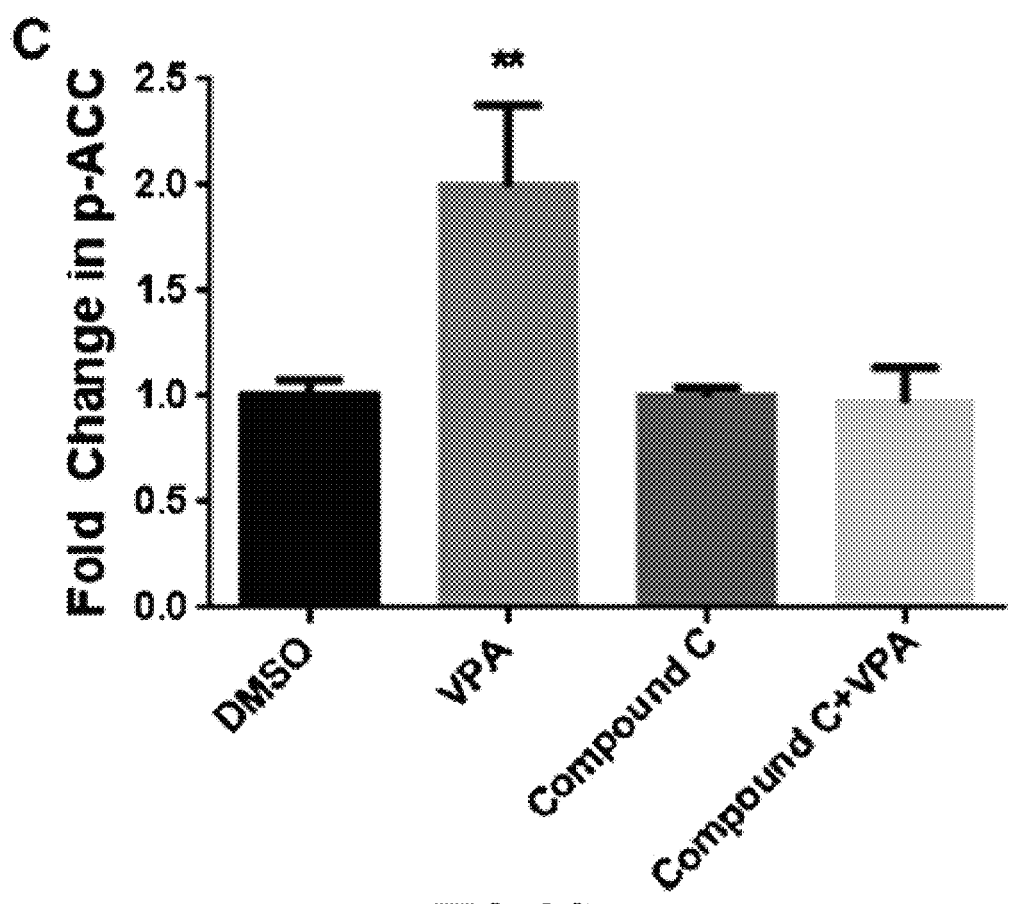
Figure 3A:
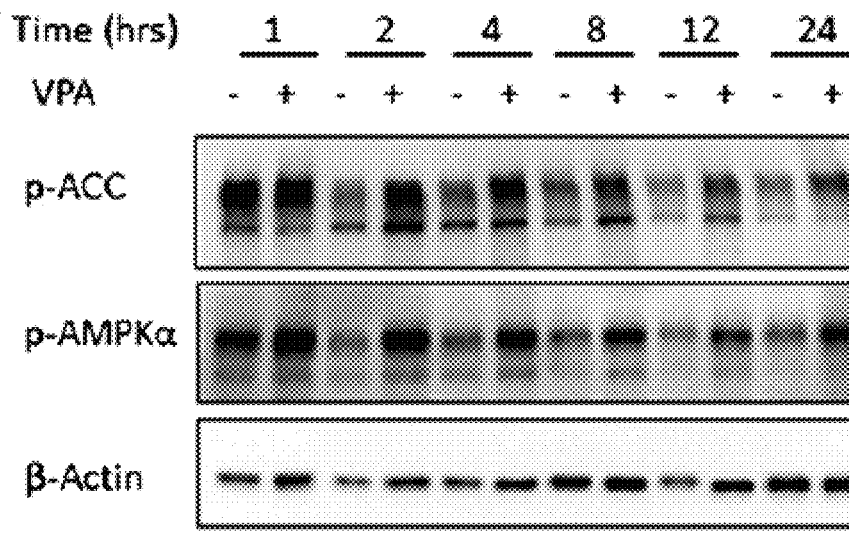
FIG. 3A-3D. VPA treatment results in increased levels of phosphorylated AMPK/ACC in primary human hepatocytes. Primary human hepatocytes were treated with vehicle or 800 mM VPA for the indicated time points and immunoblotted for p-AMPKa, AMPKa, p-ACC, ACC, and b-actin (A-D). Results are shown for four individual human hepatocyte preparations isolated from nonliving donors: (A) female, 59 years old; (B) female, 43 years old; (C) male, 36 years old, and (D) male, 55 years old.
Figure 3B:
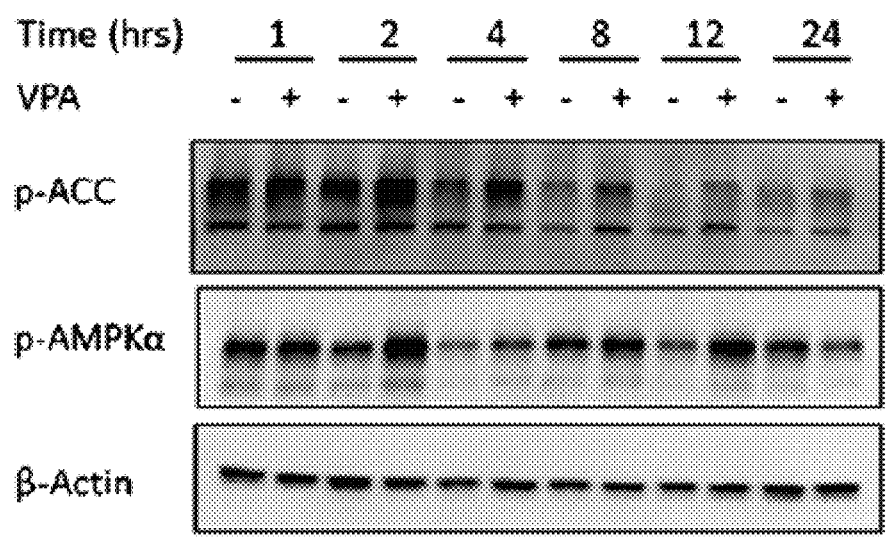
Figure 3C:
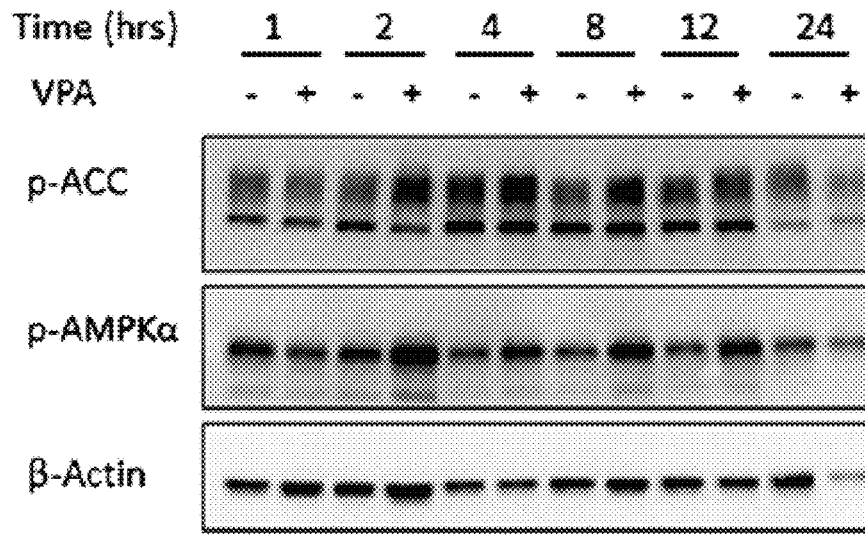
Figure 3D:
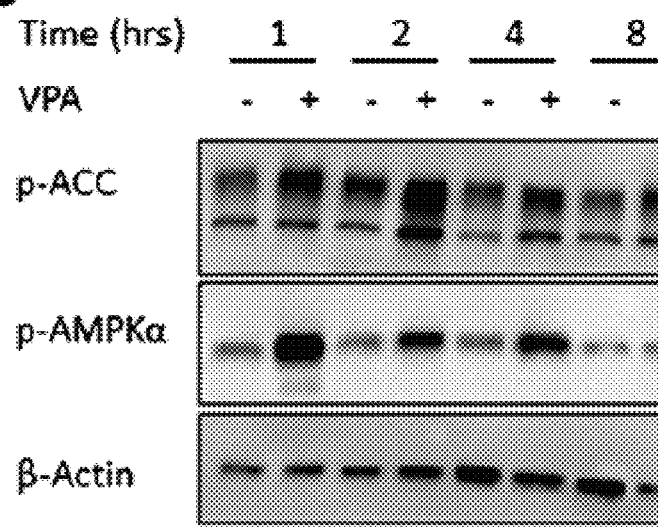

To examine the effect of VPA on AMPK phosphorylation status, we treated primary mouse hepatocytes with 800 mMVPA over a time course of 1, 2, 4, 8, 12, and 24 hours. Phosphorylation (Thr172)/activation of AMPK was observed following 1 hour of treatment with VPA. AMPK protein levels did not change significantly as a result of VPA treatment (FIG. 1A). The phosphorylation (Ser79) of ACC, indicative of its inactivation, was also observed in the presence of VPA (FIG. 1B). ACC protein levels were not significantly different following VPA treatment. To test if the phosphorylation of AMPK and ACC was dose-dependent, primary mouse hepatocytes were treated with concentrations of VPA ranging from 200 mM to 2 mM, and maximal phosphorylation of AMPK and ACC was observed at 800 mM VPA (FIG. 1C). Circulating plasma concentrations of VPA following dosing have been reported to be 400-1000 mM (Sztajnkrycer, 2002; Silva et al., 2008). To determine whether phosphorylation of ACC stimulated by VPA treatment was dependent on AMPK activation, we pretreated mouse hepatocytes with a small-molecule inhibitor of AMPK: Compound C. The presence of Compound C abrogated the phosphorylation of ACC (FIG. 2).

To test whether activation of AMPK by VPA was conserved in humans, primary human hepatocytes were treated with 800 mM VPA for 1 to 24 hours. In each of the four donors employed, phosphorylation of AMPK and ACC was observed following 1 hour of treatment with VPA (FIG. 3). Since the concentration and incubation time for stimulation of AMPK/ACC phosphorylation by VPA in primary human hepatocytes paralleled those observed using primary mouse hepatocytes we performed all subsequent studies using primary mouse hepatocytes.

Cytochrome P450-Dependent Metabolites of VPA Contribute to AMPK Activation.

Figure 4A:
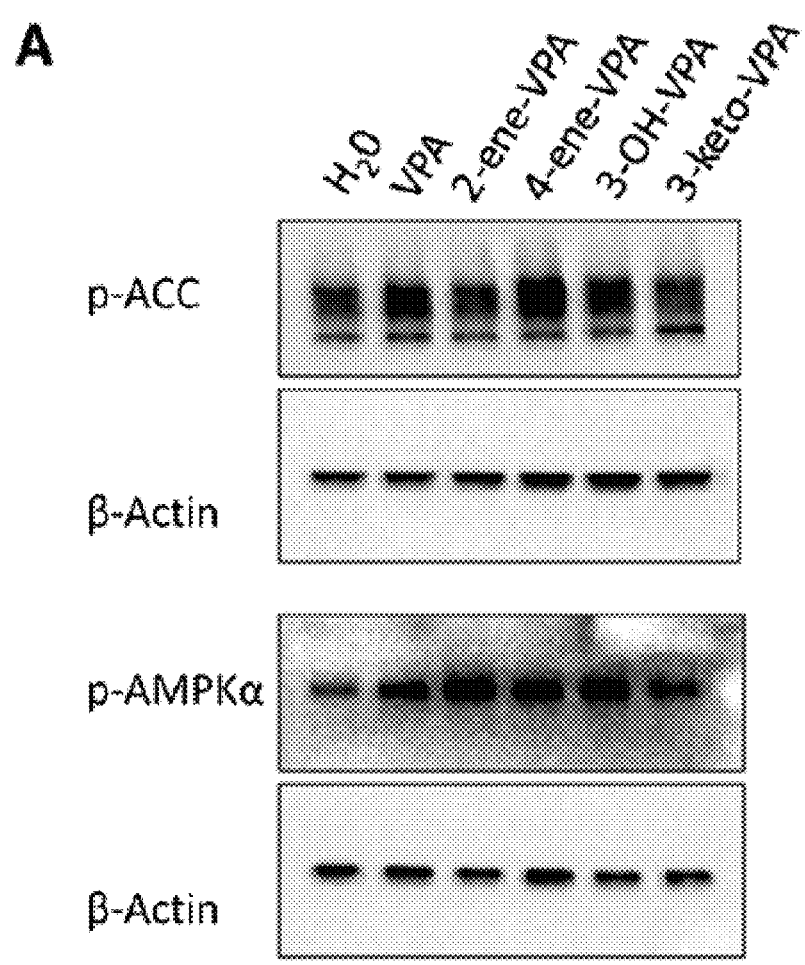
FIG. 4A-4C. Metabolites of VPA contribute to VPA-mediated AMPK/ACC phosphorylation. Primary mouse hepatocytes were treated with either vehicle, 800 mM VPA, or 20 mM of 2-ene-VPA, 4-ene-VPA, 3-OH-VPA, or 3-keto-VPA for 2 hours (A). Hepatocytes were incubated with 1 mM of ABT for 1 hour prior to treatment with 800 mM VPA for 2 hours (B). Immunoblots shown in A and B are representative of four independent experiments. Densitometry analyses were performed and are reported as the mean 6 S.D. of samples from four independent experiments using the treatment combinations indicated in C. Student's t tests were performed comparing the fold change of VPA versus vehicle and the fold change of ABT+VPA versus ABT alone to determine significance. *P , 0.05; **P, 0.01. DMSO, dimethylsulfoxide.
Figure 4B:
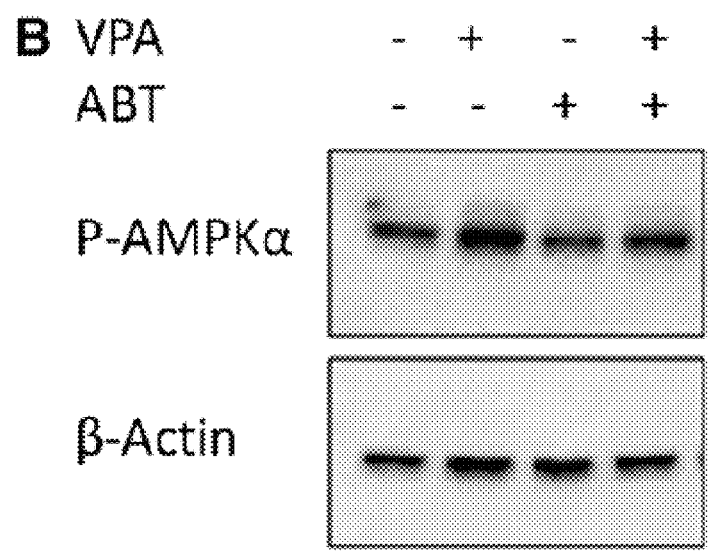
Figure 4C:
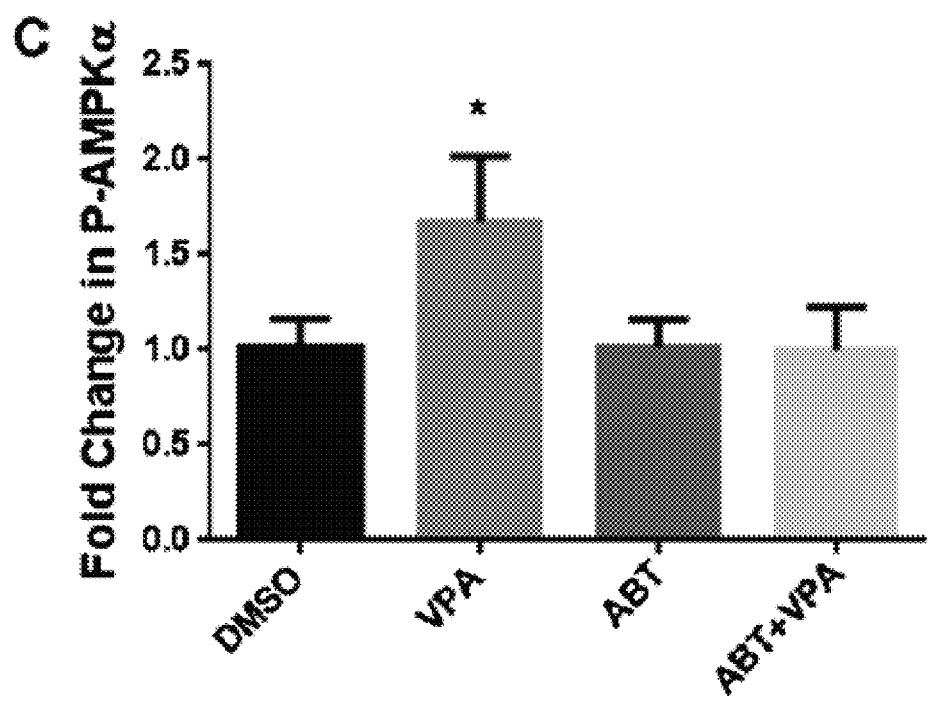

Since VPA is extensively metabolized by the cytochromes P450 and via b-oxidation, we sought to examine the phosphorylation of AMPK and ACC following treatment of primary mouse hepatocytes with metabolites of VPA. The cytochromes P450 have been shown to form the 4-ene-VPA and 3-OH-VPA metabolites, whereas 2-ene-VPA ad 3-OH-VPA metabolites result from b-oxidation. 3-Keto-VPA is formed by dehydrogenation of the cytochrome P450 formation of 3-OH-VPA (Kiang et al., 2011). Primary mouse hepatocytes were incubated with 20 mM of 2-ene-VPA, 4-ene-VPA, and 3-OH-VPA and compared with a vehicle treated control (FIG. 4A). Interestingly, treatment with the metabolites of VPA resulted in levels of phosphorylated AMPK/ACC that were greater than treatment with VPA itself, and this was most notable for 4-ene-VPA, a cytochrome P450-dependent metabolite. Treatment with a higher concentration (100 mM) of 2-ene-VPA, 4-ene-VPA, and 3-OH-VPA resulted in levels of phosphorylated AMPK/ACC that were commensurate with those observed using 20 mM of metabolites (data not shown). To test whether activation of AMPK by VPA required cytochrome P450-dependent metabolism, 1-aminobenzotriazole (ABT), an irreversible inhibitor of the cytochrome P450 superfamily of enzymes, was employed. Levels of phosphorylated AMPK were not elevated in samples treated with both ABT and VPA as compared with those incubated with ABT alone (FIGS. 4, B and C).

HDAC Inhibition by VPA and Its Metabolites.

It has been previously demonstrated in yeast and HepG2 cells (a hepatocarcinoma cell line) that the activity of AMPK is regulated by HDAC1 (Lin et al., 2012). Deacetylation of AMPK by HDAC1 was shown to facilitate its interaction with upstream kinases, thereby stimulating the phosphorylation and activation of AMPK. With these findings in mind, since VPA has been identified as an HDAC1 inhibitor (Phiel et al., 2001), it might be expected that treatment of hepatocytes with VPA would inhibit the phosphorylation/activation of AMPK via diminishing HDAC1 activity, which would be in opposition to the activation of AMPK that we have observed. Although regulation of AMPK activity by histone deacetylases has yet to be demonstrated in primary mouse or human hepatocytes, we sought to examine the HDAC inhibitory activity of both VPA and its primary metabolites and their effect on AMPK acetylation in liver/hepatocytes at the concentrations that we found increased the levels of phosphorylated AMPK/ACC.

Figure 5A:
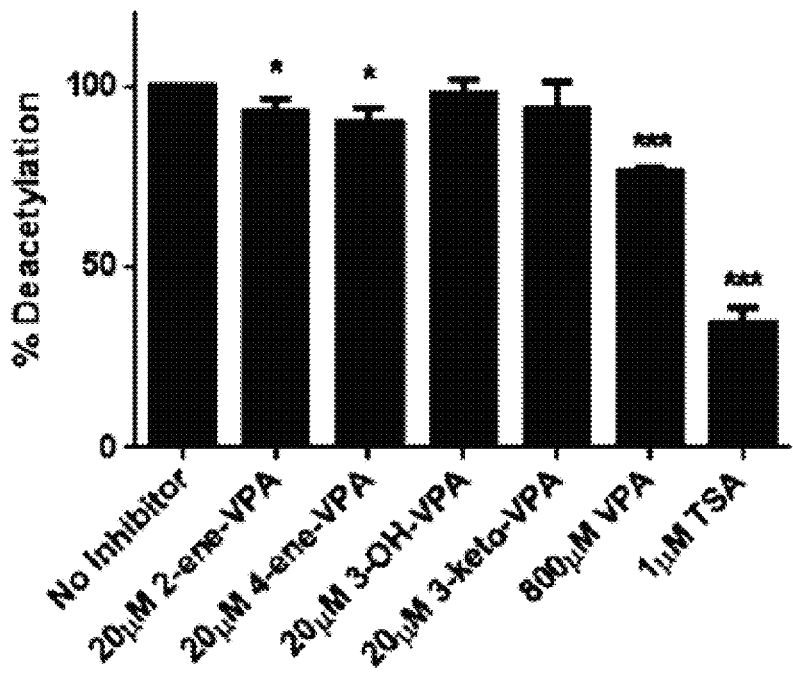
FIG. 5A-5D. Examination of HDAC inhibition by VPA and VPA metabolites. HDAC activity in the presence of vehicle; 800 mM VPA; 1 mM TSA; or 20 mM of 2-ene-VPA, 4-ene-VPA, 3-OH-VPA, or 3-keto-VPA was assessed using crude nuclear extracts prepared from mouse hepatocytes (A) and human recombinant HDAC1 (B). Deacetylation was measured using a fluorimetric assay. Dose-dependence of VPA metabolite inhibition of human recombinant HDAC1 at 20, 100, and 500 mM, and 1 or 2 mM for each metabolite (note: only 20 mM-1 mM was used for 2-ene-VPA) (C). AMPKa was immunoprecipitated and immunoblotted for AMPKa and acetylated lysine (D). Immunoblots shown in D are representative of three independent experiments. Data in graphs are reported as the mean 6 S.D. of samples from four independent experiments. Student's t tests were performed (vehicle versus VPA or metabolite-treated samples) to determine significance. *P, 0.05; ***P, 0.001. DMSO, dimethylsulfoxide.
Figure 5B:
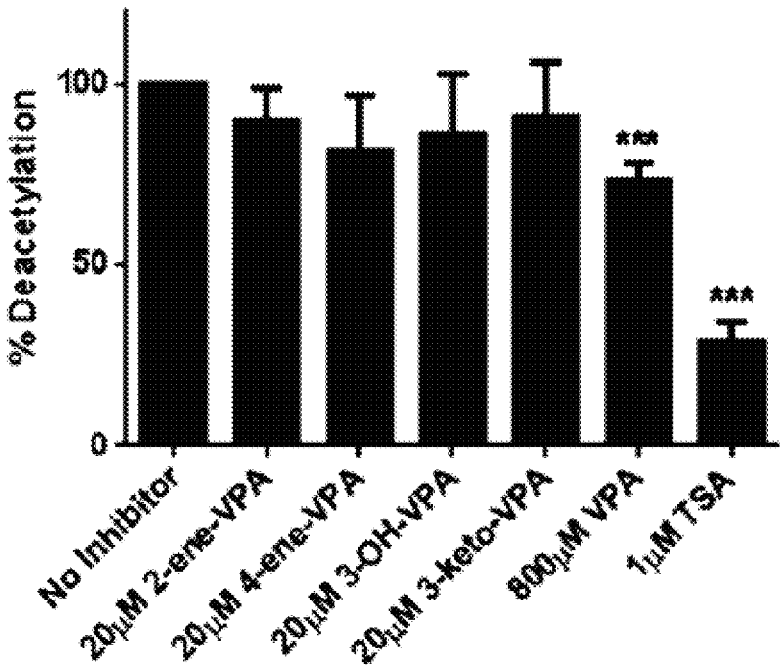
Figure 5C:
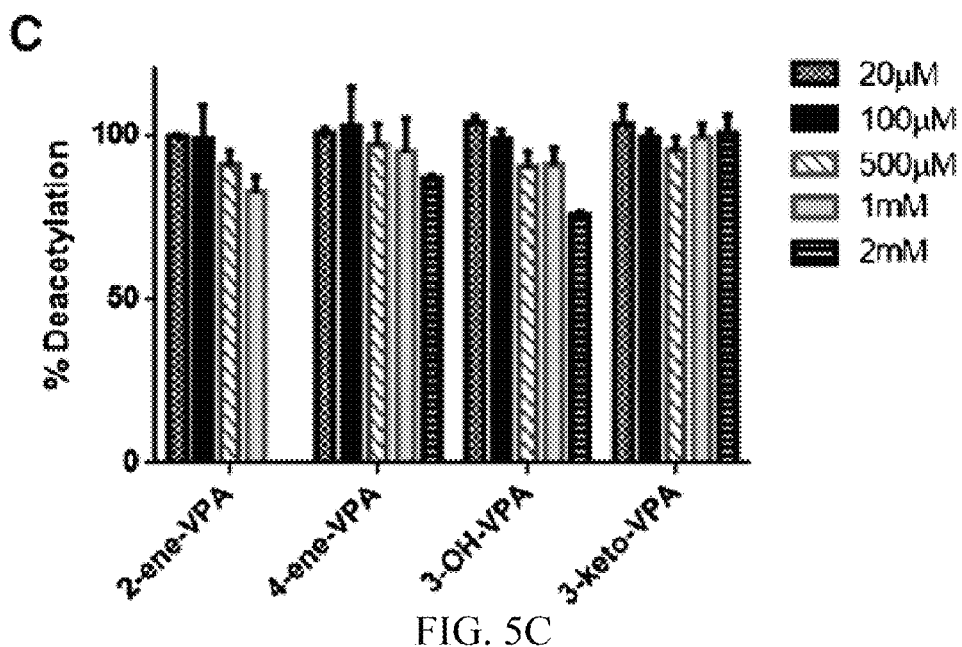
Figure 5D:
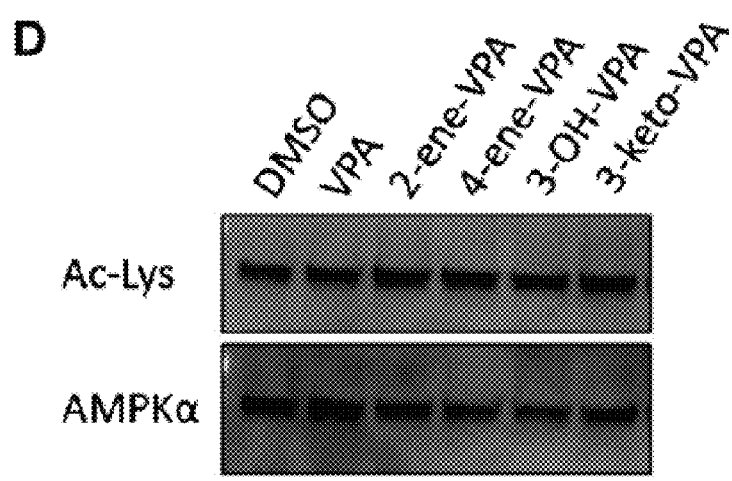

In crude nuclear extracts prepared from mouse liver, 2-ene-VPA, 4-ene-VPA, 3-OH-VPA, 3-keto-VPA, VPA, and trichostatin A (TSA) resulted in 93.6±3.6, 90.1±3.9, 98±3.9, 94±7.3, 76.4±1.2, and 34.6±4.3% deacetylation, respectively, as compared with samples treated with vehicle only (FIG. 5A). TSA is an establishedHDAC1 inhibitor and served as a positive control (Phiel et al., 2001). Using purified human recombinant HDAC1, 2-ene-VPA, 4-ene-VPA, 3-OH-VPA, 3-keto-VPA, VPA, and TSA resulted in 90±9.1, 81.5±15.5, 86±16.8, 90.9±15.2, 73.2±5, and 28.9±5.5% deacetylation, respectively (FIG. 5B). Inhibition of human recombinant HDAC1 activity by VPA metabolites was also not observed using concentrations ranging from 20 μM to 2 mM (FIG. 5C). Only inhibition of HDAC1 by VPA (P<0.001) and TSA (P<0.001) were found to be statistically significant as compared with samples treated with vehicle only; however, VPA did not completely inhibit HDAC1 as deacetylase activity was still present. VPA inhibited the deacetylase activity (P,<0.001) of both mouse liver nuclear extracts and human recombinant HDAC1 while of the metabolites of VPA, only 2-ene-VPA and 4-ene-VPA diminished deacetylase activity (P,<0.05). This was only observed using the mouse liver nuclear extracts; however, in all instances greater than 70% of the acetylation activity was remaining. In light of this, we examined the impact of VPA on AMPK acetylation status in hepatocytes via immunoprecipitation of AMPKa followed by immunoblotting for acetylated lysines (FIG. 5D). Acetylation of AMPKa in the vehicle treatment samples was commensurate with that of the samples' treatment with VPA and metabolites of VPA.

Treatment of ob/ob Mice with VPA Reduced Liver Mass/Fat Content, and Serum Glucose.

Figure 6A:
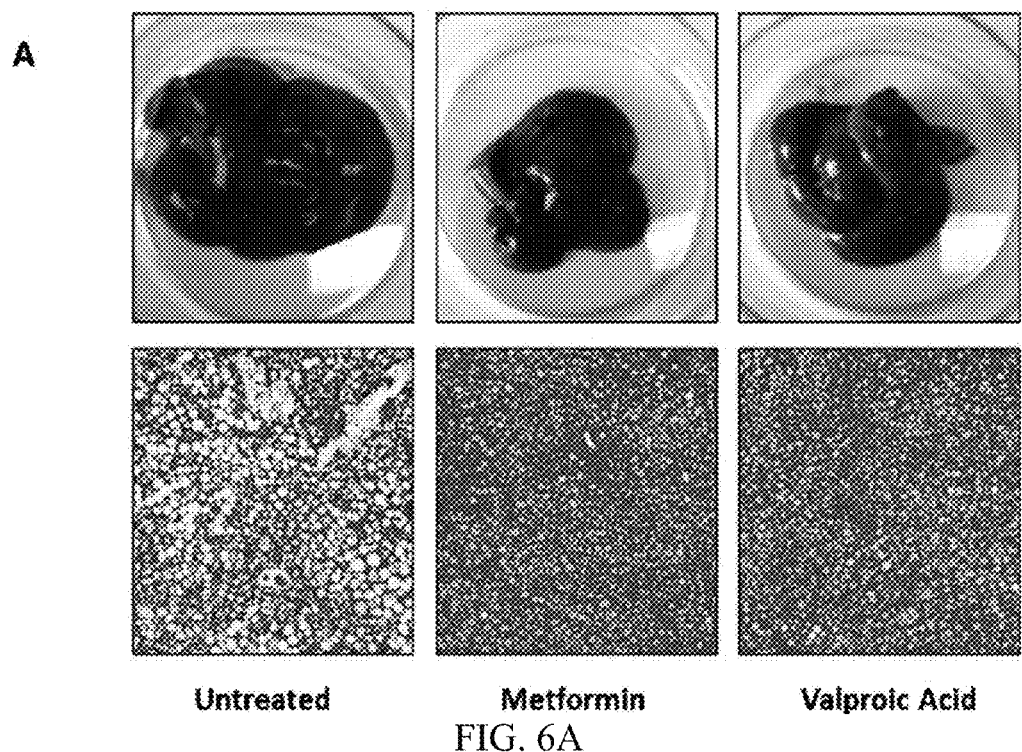
FIG. 6A-6E. Chronic administration of VPA to ob/ob mice results in decreased liver mass, hepatic lipid accumulation, and serum glucose. Ob/ob mice were administered 0.26% (w/v) VPA, 0.5% (w/v) metformin, or untreated water via their drinking water for 14 days. A section of each liver was analyzed using hemotoxylin and eosin staining Histology images are representative of four mice per treatment group (A). The mass of each liver was measured and calculated as a ratio to body mass (B). Serum glucose (C) and serum triglyceride (D) concentrations were measured using colorimetric assays. ALT was measured using a colorimetric assay to assess for hepatotoxicity (E). Data in graphs are reported as the mean 6 S.D. of four mice per cohort. Student's t tests were performed (untreated versus VPA- or metformin-treated) to determine significance. *P, 0.05; **P, 0.01.
Figure 6B:
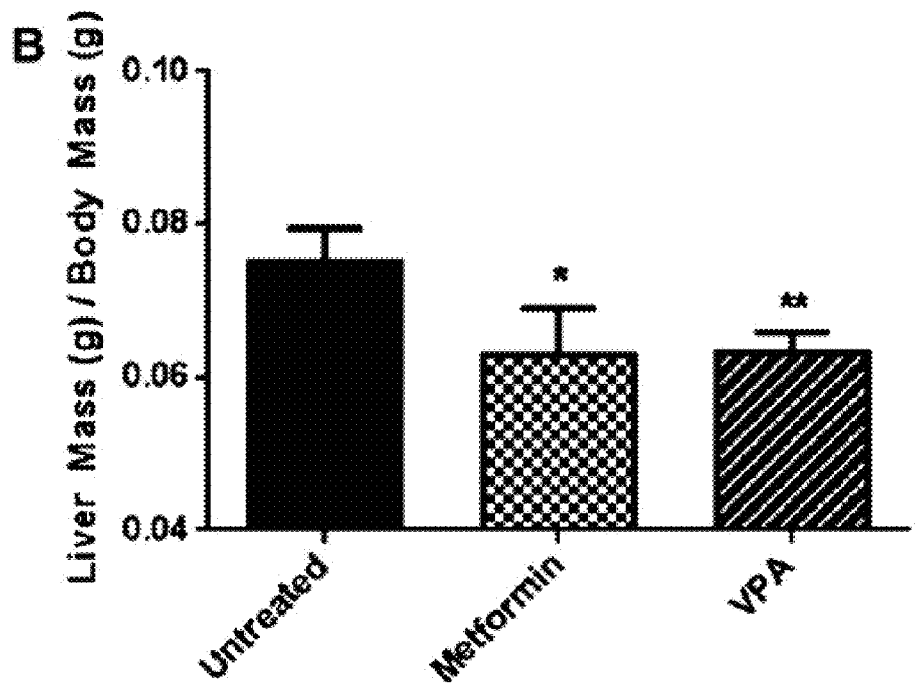
Figure 6C:
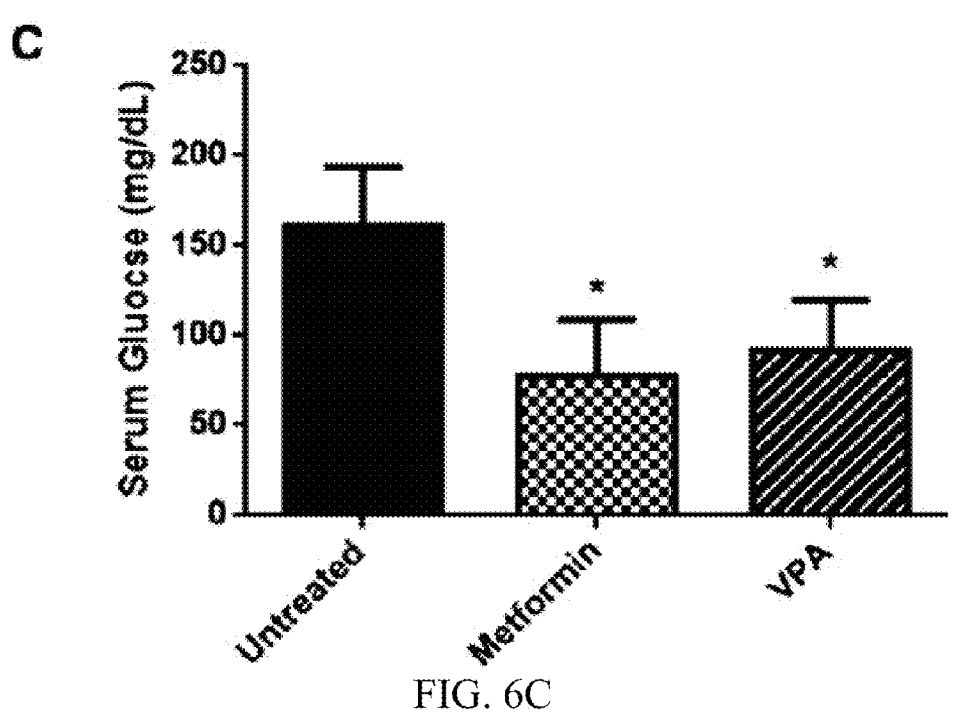
Figure 6D:
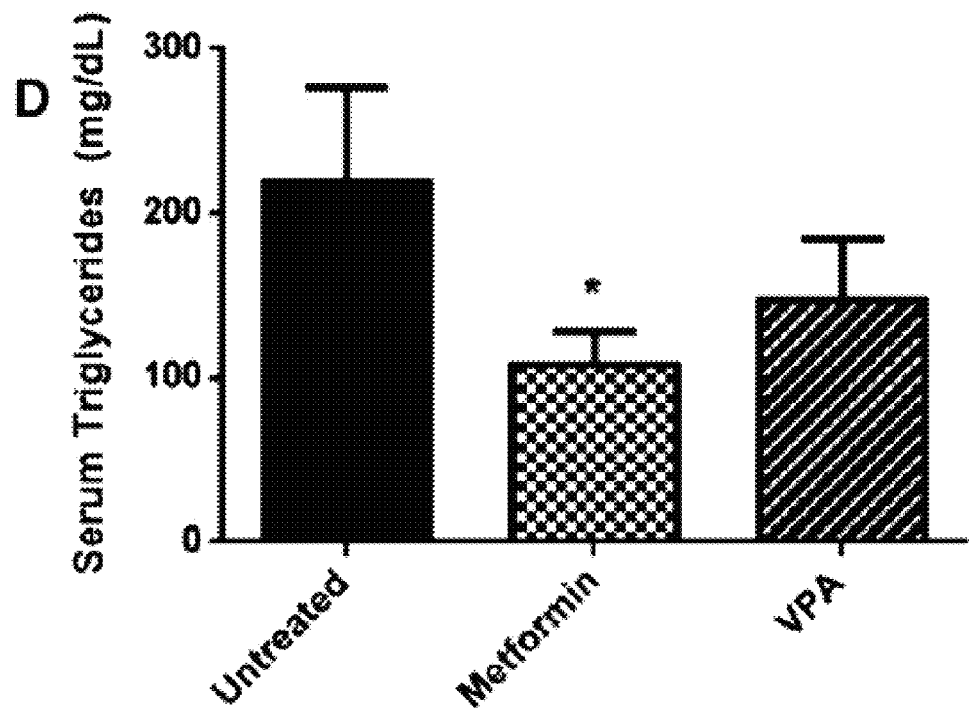
Figure 6E:
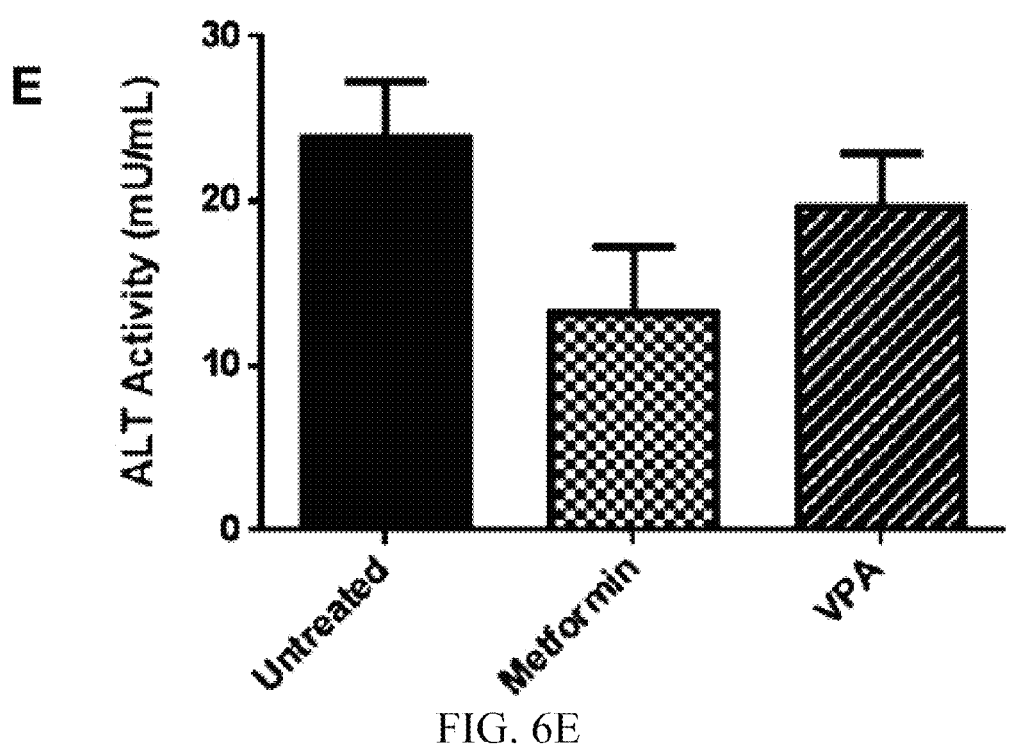

Following the observation that VPA treatment of both human and mouse primary hepatocytes results in the activation of AMPK, we sought to test whether VPA may have in vivo efficacy toward improving the obese phenotype of ob/ob mice. These mice are a useful animal model for studying metabolic disorders due to the fact that they exhibit hyperglycemia, insulin resistance, fatty liver, and rapid weight gain (Drel et al., 2006). Body masses were recorded on days 1, 7, and 14 and were 50.5±2.4, 53.2±2.5, and 55.6±2.7 g for the untreated mice; 45.4±6, 47.4±5.6, and 50±6.1 g for the metformin-treated mice; and 50.2±3, 51.8±3, and 53.8±2.7 g for the VPA-treated mice, respectively. Interestingly, only the untreated mice exhibited a significant increase in body mass from day 1 to day 14 (P=0.03). Sections of each liver were also fixed and stained with hematoxylin and eosin. The histology of the metformin and VPA-treated groups revealed a marked reduction in the accumulation of fats in the liver as compared with the untreated mice (FIG. 6A). Excision of livers from each mouse revealed that the ratio of liver mass to body mass was significantly decreased in the metformin (P=0.017) and VPA (P=0.004) treatment groups as compared with untreated mice (FIG. 6B). The serum from each treatment group was analyzed for glucose concentrations, triglyceride concentrations, and alanine aminotransaminase. Serum glucose concentrations were significantly decreased in both metformin (P=0.01) and VPA (P=0.018) treatment groups as compared with untreated mice (FIG. 6C). Serum triglyceride concentrations were also decreased in the metformin treatment group (P=0.011) and showed a trend toward a decrease in the VPA treatment group as compared with untreated mice (FIG. 6D); however, this did not reach statistical significance. Since VPA has been associated with hepatotoxicity in vivo, we measured serum activity of alanine aminotransaminase (ALT), a biomarker for hepatotoxicity. In the untreated, metformin-treated, and VPA-treated groups, ALT activity was measured at 23.8±3.4, 13.3±4, 17.7±3.2, and 17.7±14.5 mU/ml, respectively (FIG. 6E). These values are all within the range of normal and indicate that VPA did not induce hepatotoxicity in these mice.

uHPLC-MS/MS-Targeted Metabolomics.

Figure 7:
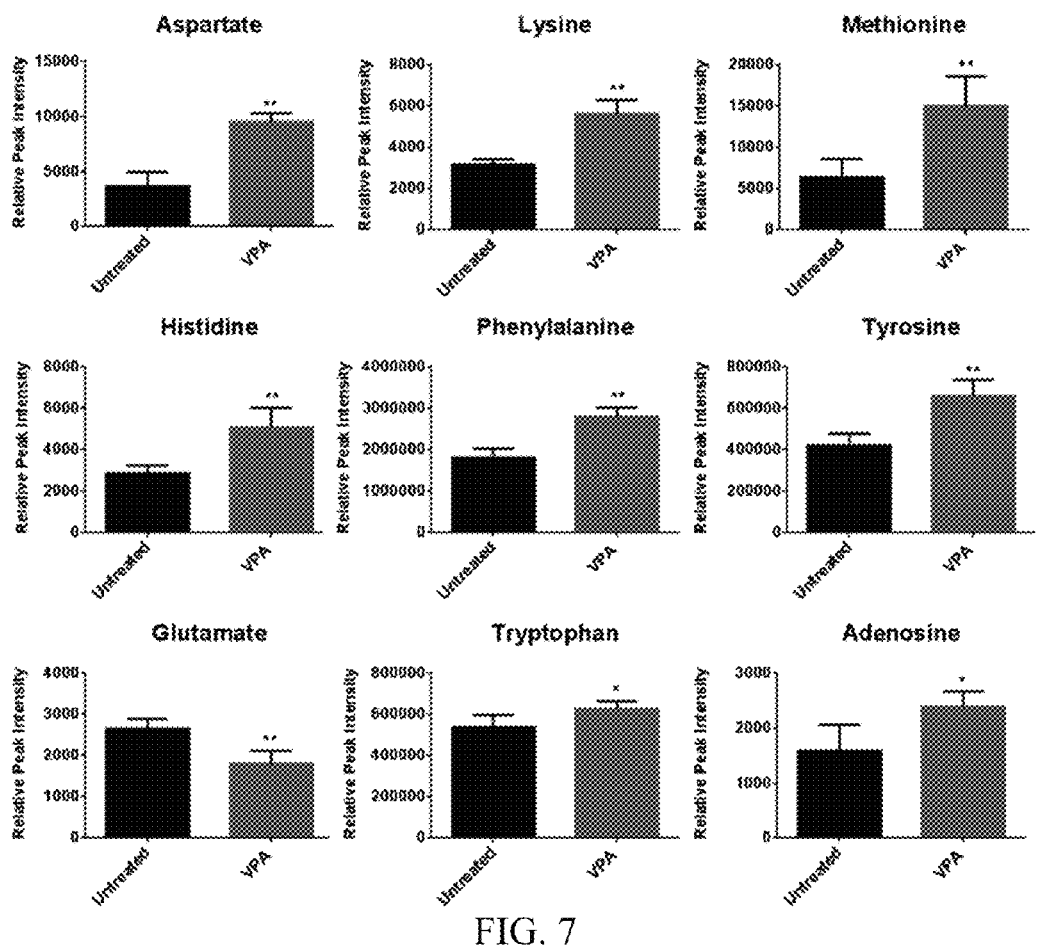
FIG. 7. uHPLC-MS/MS-targeted metabolomics analysis of ob/ob mouse serum following chronic administration of VPA. Serum was obtained on day 14 by centrifugation of whole blood and was extracted by acetonitrile protein precipitation for uHPLC-MS/MS analysis. Of the 32 endogenous small molecules that were screened, 22 were detectable in serum, and of these, 9 endogenous metabolites exhibited significant differences among treatment groups. The relative abundance of each metabolite was detected in selected reaction monitoring mode using either positive or negative ionization. The transitions that were used for each analyte are listed in Table 1. Data in graphs are reported as the mean 6 S.D. relative abundance of each metabolite for four mice per cohort. Student's t tests were performed (untreated versus VPA-treated) to determine significance. *P , 0.05; **P, 0.01.

An uHPLCMS/MS assay was developed to probe for differences in the abundance of 32 endogenous small molecules using a targeted approach. Specific targeting of metabolites of interest results in greater sensitivity and selectivity as compared with detection using a global approach. The small-molecule metabolites were chosen based on their involvement in critical biochemical pathways involved in cellular metabolism. Of the 32 compounds screened, 22 of these compounds were detectable in the serum of the ob/ob mice. Differences in the relative levels of nine of these small molecules were observed in the serum of the VPA-treated mice when compared with the untreated mice. Significant increases were detected for aspartate, lysine, methionine, histidine, phenylalanine, tyrosine, tryptophan, and adenosine for the VPA-treated mice. Decreased relative levels of glutamate were also noted in the VPA-treated mice as compared with the untreated control mice (FIG. 7).

Discussion

VPA has been used in therapy for decades for a multitude of disorders; however, to date it has yet to be demonstrated to activate AMPK. Using primary mouse hepatocytes, we have demonstrated that VPA treatment increases the levels of phosphorylated AMPK and ACC, and also that the phosphorylation of ACC was dependent on AMPK activity. In addition, we found that this effect was conserved in primary human hepatocytes, which showed similar time and concentration dependence. Because of the conservation of AMPK/ACC phosphorylation in mouse and human, we were able to use the primary mouse hepatocyte model in our subsequent studies.

Treatment of primary mouse and human hepatocytes with 800 $\mu$M of VPA resulted in increased levels of phosphorylation AMPK/ACC. VPA is often dosed at 10 mg/kg/day in adults, which results in 400-1000 $\mu$M serum concentrations (Sztajnkrycer, 2002; Silva et al., 2008). This concentration range has been found effective for the treatment of epilepsy, migraines, and bipolar disorders (Depakote package insert; AbbVielnc., North Chicago, Ill.). The time and concentration-dependence of AMPK/ACC phosphorylation in primary mouse hepatocytes following treatment with VPA is similar to that which has been reported for metformin (Foretz et al., 2010). Of note, two of the four primary human hepatocyte donors exhibited elevated levels of phosphorylated AMPK/ACC following 1 hour of treatment with either vehicle (water) or VPA, and this subsided by 4 hours. These data indicate that there may have been basal activation of AMPK at the earliest time point in these two hepatocyte preparations and not in the other donors. Phosphorylation of AMPK/ACC in primary hepatocytes was stimulated using lower concentrations of the metabolites of VPA than were required for VPA itself, indicating that the metabolites may be more potent activators of this pathway than the parent compound. This was most notable for 4-ene-VPA, a cytochrome P450-dependent metabolite. Further, the presence of the cytochrome P450 inhibitor ABT blocked the VPA-stimulated increase in the levels of phosphorylated AMPK, indicating that biotransformation of VPA is required for this effect. The metabolites of VPA evaluated in this study have been previously shown to have approximate maximal serum concentrations of 20 $\mu$M (Nau and Löscher, 1982; Acheampong et al., 1983). With this in mind, this was the concentration employed for each of the metabolites in the present study. Interestingly, this is the first study to the best of our knowledge to test a role for drug metabolites in the activation of AMPK. While metabolism of VPA in humans versus mice may ultimately differ, the metabolites examined in this study (2-ene-VPA, 4-ene-VPA, 3-OH-VPA, and 3-keto-VPA) have been previously detected in the serum of both mice and humans following dosing of VPA (Nau and Löscher, 1982, 1984; Acheampong et al., 1983).

Since VPA is a known inhibitor of HDAC1 (Phiel et al., 2001), which has been previously shown to regulate AMPK phosphorylation/activation (Lin et al., 2012), our data demonstrating that treatment with VPA resulted in increased levels of phosphorylated AMPK were potentially in conflict with this finding. We found that although inhibition of deacetylase activity was observed following treatment of mouse nuclear extracts and human recombinant HDAC1 with VPA, the acetylation of AMPK in primary mouse hepatocytes was unchanged following treatment with VPA as compared with vehicle treatment, indicating that any inhibition of HDAC1 activity that may have occurred as a result of VPA treatment did not impact the acetylation status of AMPK as compared with vehicle-treated control samples. Similarly, although 2-ene-VPA and 4-ene-VPA were shown to decrease the deacetylase activity of mouse nuclear extract, these metabolites did not appear to have an impact on the levels of acetylated AMPK. Of note, none of the metabolites exhibited inhibitory activity toward human recombinant HDAC1.

In addition to establishing that VPA treatment increased phosphorylation of AMPK in vitro, we found that treatment of ob/ob mice with VPA resulted in decreased liver masses, decreased lipid accumulation as determined via liver histology, and decreased serum glucose concentrations. These outcomes were commensurate with those achieved in the metformin treated mice. The effects of metformin on liver mass, hepatic fat accumulation, serum triglycerides, and serum glucose in vivo have been well documented (Zhou et al., 2001; Shaw et al., 2005; Foretz et al., 2010). Treatment with VPA resulted in a trend toward decreased serum triglycerides; however, it was not statistically significant compared with untreated mice. With regard to metformin, these endpoints have been previously demonstrated to be mediated by AMPK as a result of the ability of this kinase to modulate fatty acid oxidation and hepatic gluconeogenesis (Shaw et al., 2005); however, metformin has also been recently demonstrated to mediate these effects in an AMPK-independent manner (Hardie, 2013; Miller et al., 2013), revealing that there may be additional mechanisms which can contribute to the therapeutic mechanism of action for metformin, and therefore could also be considered for VPA. While VPA has been previously associated with hepatotoxicity in humans, in the present study we did not detect any abnormalities in the histology of VPA-treated livers, and ALT levels were commensurate with the normal range for ob/ob mice. The data presented here also support a previous finding that demonstrated that VPA treatment in rat hepatocytes affected carbohydrate and lipid metabolism, observed by a decreased rate of fatty acid synthesis, acetyl-CoA concentration, and citrate concentration (Becker and Harris, 1983). Since VPA is approved for use in the treatment of several disorders, analyses could be performed to determine whether this drug would have particular utility in treating metabolic disorders in individuals already receiving VPA for the treatment of other pathologies, including epilepsy or bipolar disorder. It should be noted that several studies have reported a positive correlation between weight gain and insulin resistance in patients receiving a VPA regimen (Verrotti et al., 2002; Wirrell, 2003; Mania et al., 2011; Nanau and Neuman, 2013). These correlations have been established via comparison of patient populations taking VPA to patient populations receiving a different drug, or alternatively by comparing patient populations taking VPA to healthy individuals. As such, a direct link to a molecular mechanism for VPA associated weight gain has not been established. In addition, it has also been suggested that the disease states of epilepsy or bipolar disorder may underlie or contribute to these clinical observations (Keck and McElroy, 2003). Taken together, these studies bring to light the fact that analyses of body weight in the same individual before and after treatment with VPA may be necessary in working toward fully understanding the impact of VPA on weight gain.

The use of targeted metabolomics has the potential to provide a greater understanding of molecular consequences and action of therapies. To explore biochemical changes resulting from VPA treatment, we employed a targeted uHPLC-MS/MS-based metabolomics screen to monitor the abundance of small-molecule metabolites in the serum of mice treated with VPA compared with the serum of untreated mice. Interestingly, we saw consistent increases in several amino acids as a result of VPA treatment compared with the untreated mice. Increased levels of both essential and nonessential amino acids (aspartate, lysine, methionine, phenylalanine, tyrosine, histidine, tryptophan) were noted, signifying increases in both amino acid production and dietary uptake in the VPA- and metformin-treated mice. In the context of AMPK activation, it is plausible that increased flux through the tricarboxylic acid cycle to stimulate the generation of ATP would result in increased formation of amino acids. Since these amino acids may be both precursors and byproduct reactions of the tricarboxylic acid cycle (Berg et al., 2002), it could also indicate increased production of amino acids for utilization in the tricarboxylic acid cycle. As AMPK activation is known to result in a decrease in ATP-consuming processes (Kemp et al., 1999) such as transcription, it is possible that the subsequent downregulation of protein synthesis would result in an accumulation of amino acids. Although these biochemical changes cannot be directly attributed to AMPK activation, the use of this metabolomics screening provides valuable insight to the chemical and biochemical changes that may result from VPA treatment.

The present study has established that the phosphorylation of AMPK/ACC is increased following VPA treatment in both mouse and human primary hepatocytes. Further, we have demonstrated marked decreases in liver mass/fat content and serum glucose in vivo in ob/ob mice in response to VPA treatment. These results paralleled those achieved in mice treated with metformin. In addition, use of a targeted mass spectrometry-based metabolomics assay revealed several small molecules with dissimilar abundance in the serum of ob/ob mice treated with VPA or metformin as compared with vehicle-treated mice. Overall, we have potentially demonstrated a novel mechanism of action for VPA.

REFERENCES

Acheampong A, Abbott F, and Burton R (1983) Identification of valproic acid metabolites in human serum and urine using hexadeuterated valproic acid and gas chromatographic mass spectrometric analysis. Biomed Mass Spectrom 10:586-595.

Becker C-M and Harris RA (1983) Influence of valproic acid on hepatic carbohydrate and lipid metabolism. Arch Biochem Biophys 223:381-392.

Berg J M, Tymoczko J L, and Stryer L (2002) Biochemistry, 5th ed, W.H. Freeman and Co., New York, N.Y.

Bonnefont J-P, Djouadi F, Prip-Buus C, Gobin S, Munnich A, and Bastin J (2004) Carnitine palmitoyltransferases 1 and 2: biochemical, molecular and medical aspects. Mol Aspects Med 25:495-520.

Bumpus N N (2011) Efavirenz and 8-hydroxyefavirenz induce cell death via a JNK and BimEL-dependent mechanism in primary human hepatocytes. Toxicol Appl Pharmacol 257:227-234.

Cotariu D, Evans S, Zaidman J L, and Marcus O (1990) Early changes in hepatic redox homeostasis following treatment with a single dose of valproic acid. Biochem Pharmacol 40:589-593.

Drel V R, Mashtalir N, Ilnytska O, Shin J, Li F, Lyzogubov VV, and Obrosova IG (2006) The leptin-deficient (ob/ob) mouse: a new animal model of peripheral neuropathy of type 2 diabetes and obesity. Diabetes 55:3335-3343.

Foretz M, Hébrard S, Leclerc J, Zarrinpashneh E, Soty M, Mithieux G, Sakamoto K, Andreelli F, and Viollet B (2010) Metformin inhibits hepatic gluconeogenesis in mice independently of the LKB1/AMPK pathway via a decrease in hepatic energy state. J Clin Invest 120:2355-2369.

Hardie D G (2013) AMPK: a target for drugs and natural products with effects on both diabetes and cancer. Diabetes 62:2164-2172.

Hsu M-H, Savas Ü, Lasker J M, and Johnson E F (2011) Genistein, resveratrol, and 5-aminoimidazole-4-carboxamide-1-b-D-ribofuranoside induce cytochrome P450 4F2 expression through an AMP-activated protein kinase-dependent pathway. J Pharmacol Exp Ther 337:125-136.

Kahn B B, Alquier T, Carling D, and Hardie D G (2005) AMP-activated protein kinase: ancient energy gauge provides clues to modern understanding of metabolism. Cell Metab 1:15-25.

Keck P E and McElroy S L (2003) Bipolar disorder, obesity, and pharmacotherapy associated weight gain. J Clin Psychiatry 64:1426-1435.

Kemp B E, Mitchellhill K I, Stapleton D, Michell B J, Chen Z-P, and Witters L A (1999) Dealing with energy demand: the AMP-activated protein kinase. Trends Biochem Sci 24:22-25.

Kiang T K L, Teng X W, Surendradoss J, Karagiozov S, Abbott F S, and Chang T K H (2011) Glutathione depletion by valproic acid in sandwich-cultured rat hepatocytes: Role of biotransformation and temporal relationship with onset of toxicity. Toxicol Appl Pharmacol 252:318-324.

Lade J M, Avery L B, and Bumpus N N (2013) Human biotransformation of the nonnucleoside reverse transcriptase inhibitor rilpivirine and a cross-species metabolism comparison. Antimicrob Agents Chemother 57:5067-5079.

Lee P, Peng H, Gelbart T, and Beutler E (2004) The IL-6- and lipopolysaccharide induced transcription of hepcidin in HFE-, transferrin receptor 2-, and b 2-microglobulin-deficient hepatocytes. Proc Natl Acad Sci USA 101:9263-9265.

Lin Y Y, Kiihl S, Suhail Y, Liu S-Y, Chou Y H, Kuang Z, Lu J Y, Khor C N, Lin C-L, and Bader J S et al. (2012) Functional dissection of lysine deacetylases reveals that HDAC1 and p300 regulate AMPK. Nature 482:251-255.

Ma T C, Buescher J L, Oatis B, Funk J A, Nash A J, Carrier R L, and Hoyt K R (2007) Metformin therapy in a transgenic mouse model of Huntington's disease. Neurosci Lett 411:98-103.

Mania M, Kasradze S, and Okujava N (2011) Valproic Acid related metabolic syndrome in patients with epilepsy. Georgian Med News 194:43-47.

Miller R A, Chu Q, Xie J, Foretz M, Viollet B, and Birnbaum M J (2013) Biguanides suppress hepatic glucagon signalling by decreasing production of cyclic AMP. Nature 494:256-260.

Nanau R M and Neuman M G (2013) Adverse drug reactions induced by valproic acid. Clin Biochem 46:1323-1328.

Nau H and Löscher W (1984) Valproic acid and metabolites: pharmacological and toxicological studies. Epilepsia 25 (Suppl 1):S14-S22.

Nau H and Löscher W (1982) Valproic acid: brain and plasma levels of the drug and its metabolites, anticonvulsant effects and gamma-aminobutyric acid (GABA) metabolism in the mouse. J Pharmacol Exp Ther 220: 654-659.

Phiel C J, Zhang F, Huang E Y, Guenther M G, Lazar M A, and Klein P S (2001) Histone deacetylase is a direct target of valproic acid, a potent anticonvulsant, mood stabilizer, and teratogen. J Biol Chem 276:36734-36741.

Phoenix K N, Vumbaca F, and Claffey K P (2009) Therapeutic metformin/AMPK activation promotes the angiogenic phenotype in the ER alpha negative MDA-MB-435 breast cancer model. Breast Cancer Res Treat 113:101-111.

Shaw R J, Lamia K A, Vasquez D, Koo S-H, Bardeesy N, Depinho R A, Montminy M, and Cantley L C (2005) The kinase LKB1 mediates glucose homeostasis in liver and therapeutic effects of metformin. Science 310:1642-1646.

Silva M F B, Aires C C P, Luis P B M, Ruiter J P N, IJlst L, Duran M, Wanders R J A, and Tavares de Almeida I (2008) Valproic acid metabolism and its effects on mitochondrial fatty acid oxidation: a review. J Inherit Metab Dis 31:205-216.

Sugai F, Yamamoto Y, Miyaguchi K, Zhou Z, Sumi H, Hamasaki T, Goto M, and Sakoda S (2004) Benefit of valproic acid in suppressing disease progression of ALS model mice. Eur J Neurosci 20:3179-3183.

Sztajnkrycer M D (2002) Valproic acid toxicity: overview and management. J Toxicol Clin Toxicol 40:789-801.

Verrotti A, Basciani F, De Simone M, Trotta D, Morgese G, and Chiarelli F (2002) Insulin resistance in epileptic girls who gain weight after therapy with valproic acid. J Child Neurol 17:265-268.

Winder W W and Hardie D G (1999) AMP-activated protein kinase, a metabolic master switch: possible roles in type 2 diabetes. Am J Physiol 277:E1-E10.

Wirrell E C (2003) Valproic acid-associated weight gain in older children and teens with epilepsy. Pediatr Neurol 28:126-129.

Zhou G, Myers R, Li Y, Chen Y, Shen X, Fenyk-Melody J, Wu M, Ventre J, Doebber T, and Fujii N et al. (2001) Role of AMP-activated protein kinase in mechanism of metformin action. J Clin Invest 108:1167-1174.

We claim:

1. A method for reducing hepatic fat accumulation and serum glucose in a subject comprising the step of administering an effective amount of valproic acid (VPA) or metabolite thereof to the subject, wherein the VPA metabolite is one or more of 2-ene-VPA, 4-ene-VPA, 3-OH-VPA, and 3-keto-VPA.

2. The method of claim 1, wherein the VPA metabolite is 4-ene VPA.

3. A method for treating obesity in a subject comprising the step of administering an effective amount of valproic acid (VPA) or metabolite thereof to the subject wherein the VPA metabolite is one or more of 2-ene-VPA, 4-ene-VPA, 3-OH-VPA, and 3-keto-VPA.

4. The method of claim 3, wherein the VPA metabolite is 4-ene VPA.

5. A method for treating type 2 diabetes in a subject comprising the step of administering an effective amount of valproic acid (VPA) or metabolite thereof to the subject, wherein the VPA metabolite is one or more of 2-ene-VPA, 4-ene-VPA, 3-OH-VPA, and 3-keto-VPA.

6. The method of claim 5, wherein the VPA metabolite is 4-ene VPA.

* * * * *